US008871940B2

(12) United States Patent
Zhu et al.

(10) Patent No.: US 8,871,940 B2
(45) Date of Patent: Oct. 28, 2014

(54) UNSYMMETRICAL BISAZIDES FOR CHEMOSELECTIVE SEQUENTIAL LIGATION

(71) Applicant: The Florida State University Reasearch Foundation, Inc., Tallahassee, FL (US)

(72) Inventors: Lei Zhu, Tallahassee, FL (US); Zhao Yuan, Tallahassee, FL (US); Gui-Chao Kuang, Shanghai (CN)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 13/941,798

(22) Filed: Jul. 15, 2013

(65) Prior Publication Data

US 2014/0018541 A1 Jan. 16, 2014

Related U.S. Application Data

(60) Provisional application No. 61/671,958, filed on Jul. 16, 2012.

(51) Int. Cl.
*C07D 215/12* (2006.01)
*C07D 403/14* (2006.01)
*C07D 401/14* (2006.01)
*C07D 401/06* (2006.01)
*C07D 403/06* (2006.01)

(52) U.S. Cl.
CPC ............ *C07D 403/14* (2013.01); *C07D 401/14* (2013.01); *C07D 401/06* (2013.01); *C07D 403/06* (2013.01)
USPC ........................................................ 546/176

(58) Field of Classification Search
None
See application file for complete search history.

(56) References Cited

PUBLICATIONS

Thomas, J. et al. J. Amer Chem Soc 2005, vol. 127, pp. 12434-12435.*
Guiard, Julie et al., "Double-Click" Protocol for Synthesis of Heterobifunctional Multivalent Ligands: Toward a Focused Library of Specific Norovirus Inhibitors, Chemistry—A European Journal, 2011, pp. 7438-7441, vol. 17, Wiley-VCH Veriag GmbH & Company.
Ingale, Sachin A. et al., Stepwise Click Functionalization of DNA through a Bifunctional Azide with a Chelating and a Nonchelating Azido Group, The Journal of Organic Chemistry, Jan. 11, 2013, pp. 6, ACS Publications.
Pujari, Suresh S. et al., Parallel Stranded DNA Stabilized with Internal Sugar Cross-links: Synthesis and Click Ligation of Oligonucleotides Containing 2'-Propargylated Isoguanosine, The Journal of Organic Chemistry, Aug. 5, 2013, ACS Publications.
Brotherton, Wendy S. et al., Apparent Copper(II)-Accelerated Azide—Alkyne Cycloaddition, Organic Letters, 2009, pp. 4954-4957, vol. 11, No. 21, American Chemical Society.
Kuang, Gui-Chao et al., Experimental Investigation on the Mechanism of CHelation-Assisted, Copper(II) Acetate-Accelerated Azide—Alkyne Cycloaddition, 2011, pp. 13984-14001, vol. 2133, ACS Publications.
Kalia, Jeet et al., Advances in Bioconjugation, National Institutes of Health, pp. 138-147, 2010, vol. 14, No. 2.
Beal, David M. et al., Click-enabled heterotrifunctional template for sequential bioconjugations, Organic & Biomolecular Chemistry, Oct. 10, 2011, pp. 548-554, vol. 10.
Aucagne, Vincent et al., Chemoselective Formation of Successive Triazole Linkages in One Pot: "Click-Click" Chemistry, Organic Letters, 2006, pp. 4505-4507, vol. 8, No. 20, American Chemical Society.
Elamari, Hichem et al., Chemoseletive preparation of disymmetric bistriazoles from bisalkynes, Tetrahedron Letters, 2011, pp. 658-660, vol. 52, Elsevier.
Kolb, Hartmuth C. et al., Click Chemistry: Diverse Chemical Function from a Few Good Reactions, Angew. Chem. Int. Ed, 2001, pp. 2005-2021, vol. 40, Wiley-VCH Verlad GmbH.
Gramlich, Phillipp M. E. et al., Click-Click-Click: Single to Triple Modification of DNA**, Angew. Chem. Int. Ed, 2008, pp. 3442-3444, vol. 47, Wiley-VCH Verlad GmbH.
Sletten, Ellen M. et al., From Mechanism to Mouse: A Tale of Two Bioorthogonal Reactions, Accounts of Chemical Research, 2011, pp. 666-676, vol. 44, No. 9, www.pubs.acs.org/accounts.
Hein, Jason E. et al., Copper-catalyzed azide cycloaddition (CuAAC) and beyond: new reactivity of copper(I) acetylides, Chem. Soc. Rev., 2010, pp. 1302-1315, vol. 39, The Royal Society of Chemistry.
Durmaz, Hakan et al., One-Pot Synthesis of ABC Type Triblock Copolymers via in situ Click [3+2] and Diels-Alder [4+2] Reactions, Macromolecules, 2007, pp. 191-198, vol. 40, American Chemical Society.
Galibert, Mathieu et al., One-Pot Approach to Well-Defined Blomolecular Assemblies by Orthogonal Chemoselective Ligations, Angew. Chem. Int. Ed., 2009, pp. 2576-2579, Wiley-VCH Verlad GmbH.
Sanders, Brian C. et al., Metal-Free Sequential [3+2] Dipolar Cycloadditions using Cyclooctynes and 1,3-Dipoles of Different Reactivity, Journal of the American Chemical Society, 2011, pp. 949-957, vol. 133, ACS Publications.
Ehlers Ina et al., Modular Synthesis of Triazole-Containing Triaryl a-Helis Mimetics, European Journal of Organic Chemical, 2011, pp. 2474-2490, Wiley-VCH Verlad GmbH.

(Continued)

*Primary Examiner* — Heidi Reese
(74) *Attorney, Agent, or Firm* — Armstrong Teasdale LLP

(57) ABSTRACT

Unsymmetrical bisazides containing chelating and non-chelating azido groups undergo chemoselective three-component copper(I)-catalyzed azide-alkyne conjugation reactions with two different alkyne molecules. In conjunction with the reactivity gap between aromatic and aliphatic alkynes, a bistriazole molecule can be generated with an excellent regioselectivity by mixing two alkynes and a bisazide in a single reaction container. This method is applicable in aqueous solutions at neutral pH, which may lend utilities in bioconjugation applications.

12 Claims, 1 Drawing Sheet

(56) References Cited

PUBLICATIONS

Kempe, Kristian et al., Three-Fold Metal-Free Efficient ("Click") Reactions onto a Multifunctional Poly(2-oxazoline) Designer Scaffold, Macromolecules, 2011, pp. 6424-6432, vol. 44, ACS Publications.

Li Long et al., One-Pot Dual-Labeling of a Protein by Two Chemoselective Reactions, Angew Chem. Int. Ed., 2011, pp. 8287-8290, vol. 50, Wiley-VCH Verlad GmbH.

Valverde, Ibai E. et al., Synthesis of a Biologically Active Triazole-Containing Analogue of Cystatin A Through Successive Peptidomimetic Alkyne-Azide Ligations, Angew. Chem. Ind. Ed., 2012, pp. 718-722, vol. 51, Wiley-VCH Verlad GmbH.

* cited by examiner

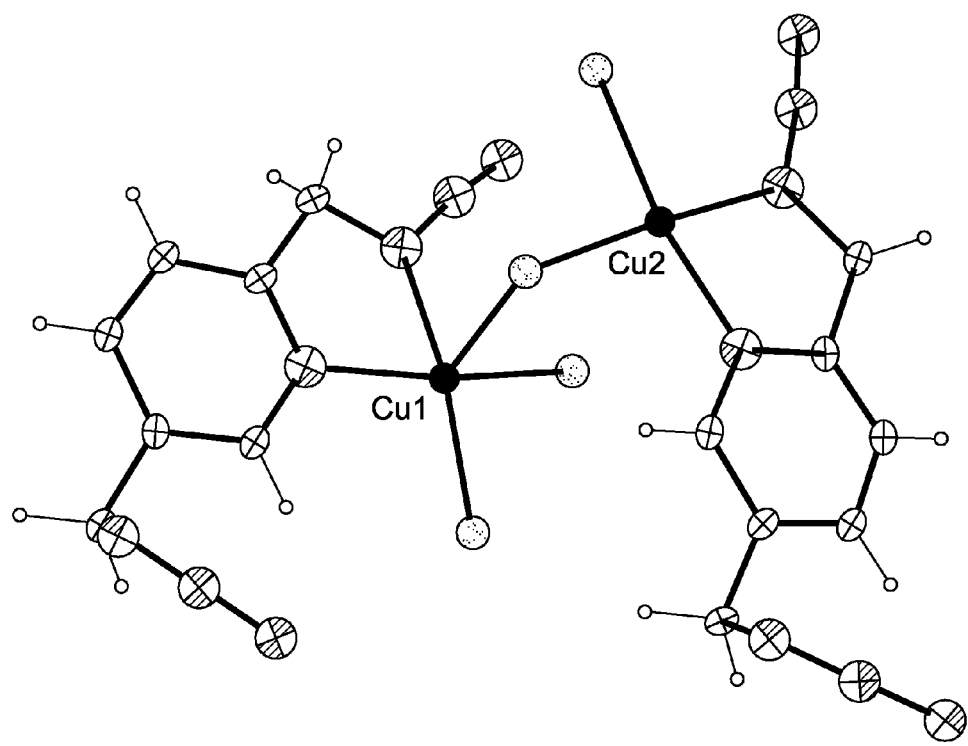

UNSYMMETRICAL BISAZIDES FOR CHEMOSELECTIVE SEQUENTIAL LIGATION

CROSS REFERENCE TO RELATED APPLICATION

This application claims priority from U.S. Provisional Application Ser. No. 61/671,958, filed Jul. 16, 2012, the disclosure of which is incorporated herein as if set forth in its entirety.

STATEMENT REGARDING FEDERALLY SPONSORED RESEARCH

This invention was made with government support under Grant No. CHE-0809201 awarded by the National Science Foundation. The government has certain rights in the invention.

FIELD OF THE INVENTION

The field of the invention relates generally to a method for preparing unsymmetrical bisazides by an azide-alkyne conjugation reaction of a bisazide with two different alkyne molecules, and more particularly to preparing unsymmetrical bisazides by an azide-alkyne conjugation reaction of a bisazide with sequential addition of two different alkyne molecules.

BACKGROUND OF THE INVENTION

Chemoselective sequential ligation has been employed in applications including multiple labeling and syntheses of macromolecular assemblages. For examples of multiple labeling applications, see (a) Gramlich, P. M. E.; Warncke, S.; Gierlich, J.; Carell, T. Angew. Chem. Int. Ed. 2008, 47, 3442; (b) Sanders, B. C.; Friscourt, F.; Ledin, P. A.; Mbua, N. E.; Arumugam, S.; Guo, J.; Boltje, T.; Popik, V. V.; Boons, G.-J. J. Am. Chem. Soc. 2011, 133, 949; and (c) Yi, L.; Sun, H.; Itzen, A.; Triola, G.; Waldmann, H.; Goody, R. S.; Wu, Y.-W. Angew. Chem. Int. Ed. 2011, 50, 8287. For examples of macromolecular assemblages applications, see (a) Durmaz, H.; Dag, A.; Altintas, O.; Erdogan, T.; Hizal, G.; Tunca, U. Macromolecules 2007, 40, 191; (b) Galibert, M.; Dumy, P.; Boturyn, D. Angew. Chem. Int. Ed. 2009, 48, 2576; (c) Kempe, K.; Hoogenboom, R.; Jaeger, M.; Schubert, U. S. Macromolecules 2011, 44, 6424; (d) Ehlers, I.; Maity, P.; Aubé, J.; König, B. Eur. J. Org. Chem. 2011, 2474; and (e) Valverde, I. E.; Lecaille, F.; Lalmanach, G.; Aucagne, V.; Delmas, A. F. Angew. Chem. Int. Ed. 2012, 51, 718. The two strategies in devising a sequential ligation are (1) successive coupling reactions of the same type that require the deprotection of the subsequent reactive site, and (2) the utilization of two or more completely different reactions. For examples of successive coupling reactions of the same type, see Gramlich et al., Ehlers et al., and Valverde et al. For examples of the utilization of two or more completely different reactions, see Sanders et al., Yi et al., Durmaz et al., Galibert et al., and Kempe et al. Recent research in bifunctional molecular linkers highlights the key challenge in developing chemoselective sequential ligation protocols, which is to achieve a complete regiochemical control of the coupling reactions in a timely and cost-effective manner, while providing broad functional group tolerance.

The copper(I)-catalyzed azide-alkyne cycloaddition (CuAAC) and its metal-free variants, which are the most widely applied "click" reactions, appear to be the methods of choice in developing bifunctional molecular linkers, due to their enormous substrate scopes and rapid reaction kinetics. See Hein, J. E.; Fokin, V. V. Chem. Soc. Rev. 2010, 39, 1302; Sletten, E. M.; Bertozzi, C. R. Acc. Chem. Res. 2011, 44, 666; and Kolb, H. C.; Finn, M. G.; Sharpless, K. B. Angew. Chem. Int. Ed. 2001, 40, 2004. Several examples of AAC-based bifunctional linkers known in the prior art are shown in the following Table 1 in which differentiating the reactivities of alkyne substrates leads to chemoselectivity in sequential ligation reactions.

TABLE 1

Unsymmetrical Bisalkyne Linkers.

| Citation | Structure |
|---|---|
| Aucagne and Leigh, 2006, compound 1 | 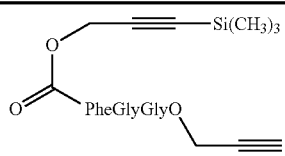 |
| Girard et al., 2011, compound 2 | 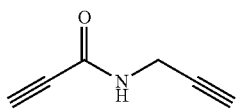 |
| Beal et al., 2012, compound 3 | 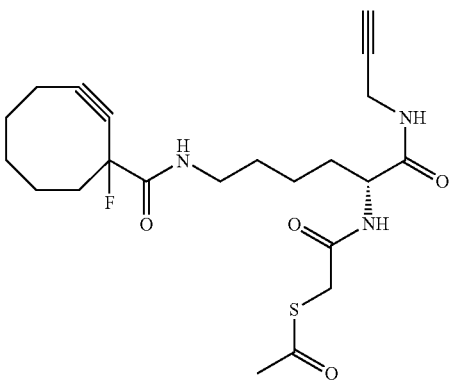 [SMILES: C#CCNC(=O)[C@@H](CCCCNC(=O)C1(F)C#CCCCCC1)NC(=O)CSC(C)=O] |

Aucagne and Leigh introduced a double-click method, in which two CuAAC reactions of compound I are spaced by a TMS-alkyne deprotection step to gain chemoselectivity. See Aucagne, V.; Leigh, D. A. Org. Lett. 2006, 8, 4505. In bisalkyne linker 2 by Girard et al., an electron-deficient propiolamide, which reacts with an azide thermally (i.e., without a copper catalyst), pairs up with a propargylic group targeted for a CuAAC reaction. See Elamari, H.; Meganem, F.; Herscovici, J.; Girard, C. Tetrahedron Lett. 2011, 52, 658. The pairing of cyclooctyne and terminal alkyne is utilized in compound 3 by Beal et al., in which the two triple bonds react via strain-promoted thermal reaction and copper(I)-catalyzed means, respectively. See Beal, D. M.; Albrow, V. E.; Burslem, G.; Hitchen, L.; Fernandes, C.; Lapthorn, C.; Roberts, L. R.; Selby, M. D.; Jones, L. H. Org. Biomol. Chem. 2012, 10, 548.

Although effective to various degrees, these earlier approaches suffer from a few limitations. The double-click method requires a protection/deprotection sequence, which adds workload. The thermal AAC reactions using strained or electron-deficient alkynes are relatively slow at rt, in addition to the lack of regioselectivity in affording 1,4- or 1,5-disubstituted triazoles. Furthermore, the propiolamide derivatives are prone to Michael addition with a nucleophile, thus limiting the scope of substrates in sequential ligations. In another noteworthy double-click method, amino-substituted organic azides are employed in which a diazo transfer reaction is required to activate the amino group to azido for the second CuAAC reaction. See Guiard, J.; Fiege, B.; Kitov, P. I.; Peters, T.; Bundle, D. R. *Chem. Eur. J.* 2011, 17, 7438.

BRIEF DESCRIPTION OF THE INVENTION

The present invention is directed to a method of preparing a bistriazole compound. The method comprises contacting a bis-azide compound and a first alkyne to thereby prepare an intermediate mono-azide/mono-triazole compound; and contacting the intermediate mono-azide/mono-triazole compound with a second alkyne to thereby prepare the bis-triazole compound. The bis-azide comprises a chelating azide and a non-chelating azide, and the first alkyne selectively reacts with the chelating azide.

BRIEF DESCRIPTION OF THE DRAWINGS

FIG. 1 depicts an ORTEP diagram of $[Cu_2(7)_2Cl_4]$ (30% ellipsoids). Crosses—carbon; blank—hydrogen; inverse triangles—nitrogen; triangles—chlorine; diamonds—copper.

DETAILED DESCRIPTION OF THE EMBODIMENT(S) INVENTION

The present invention is directed to a double-conjugation method in which two azide-alkyne cycloaddition (AAC) reactions occur sequentially in a single reaction mixture without an intervening deprotection step. Unsymmetrical bisazides containing chelating and non-chelating azido groups undergo chemoselective three-component copper(I)-catalyzed azide-alkyne conjugation reactions with two different alkyne molecules. In conjunction with the reactivity gap between aromatic and aliphatic alkynes, a bistriazole molecule can be generated with an excellent regioselectivity by mixing two alkynes and a bisazide in a single reaction container. This method is applicable in aqueous solutions at neutral pH, which may lend utilities in bioconjugation applications. In some embodiments, the method of the present invention is directed to a double-conjugation method in which two copper(I)-catalyzed azide-alkyne cycloaddition (CuAAC) reactions occur sequentially in a single reaction mixture without an intervening deprotection step. The method of the present invention affords an excellent regioselectivity while preserving the fast kinetics and large substrate scope of the CuAAC reaction.

The disclosed bisazide compounds act as effective molecular linkers to connect two ethynyl functionalized molecular or macromolecular entities rapidly under almost all conditions commonly encountered in solution chemistry. For example, two different functional units of biomacromolecules could be ligated sequentially by using this double click reaction with a bisazide linker. The bisazide linkers can also be used to combine two polymeric building blocks together to form a single copolymer in a one-pot procedure. The general reaction is shown in the following exemplary reaction sequence:

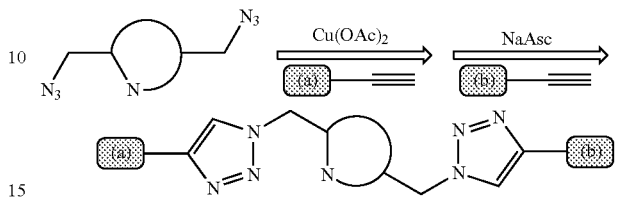

wherein (a) and (b) represent molecular or macromolecular functionality. Macromolecular functionality includes hydrocarbon polymers such as polyethylene and polypropylene, heteroaromatic polymers such as polyesters, polyamides, and polyurethanes and biological macromolecules such as peptides, proteins, nucleic acid polymers such as DNA and RNA, and polysaccharides.

Another potentially interesting utility of the bisazide linkers is the flipping of ethynyl functionality to an azido group, which is accomplished after the first "click" reaction. The copper-catalyzed azide-alkyne cycloaddition chemistry is widely applied in many fields. But there is an inherent hazard in preparing various azido-functionalized molecules. By using a commercially available bisazide linker, one can easily turn an ethynyl functionalized molecule to an azide, on demand.

The method of the present invention exploits the discovery that copper(II) acetate $(Cu(OAc)_2)$ and chelating azides possess uniquely high reactivities in CuAAC reactions. See Brotherton, W. S.; Michaels, H. A.; Simmons, J. T.; Clark, R. J.; Dalal, N. S.; Zhu, L. *Org. Lett.* 2009, 11, 4954 and Kuang, G.-C.; Guha, P. M.; Brotherton, W. S.; Simmons, J. T.; Stankee, L. A.; Nguyen, B. T.; Clark, R. J.; Zhu, L. *J. Am. Chem. Soc.* 2011, 133, 13984. The chemoselectivity may be demonstrated by chelating 2-picolylazide and a non-chelating benzylazide in the two sequential reactions with alkynes shown in Table 2. In the presence of only $Cu(OAc)_2$, the added alkyne selectively reacts with the chelating 2-picolylazide to afford triazoles A and C. The subsequent addition of sodium ascorbate increases the concentration of the copper(I) catalyst, leading to the second triazole formation (B and D) involving the non-chelating benzylazide.

TABLE 2

Azide Selectivity in CuAAC Reactions.

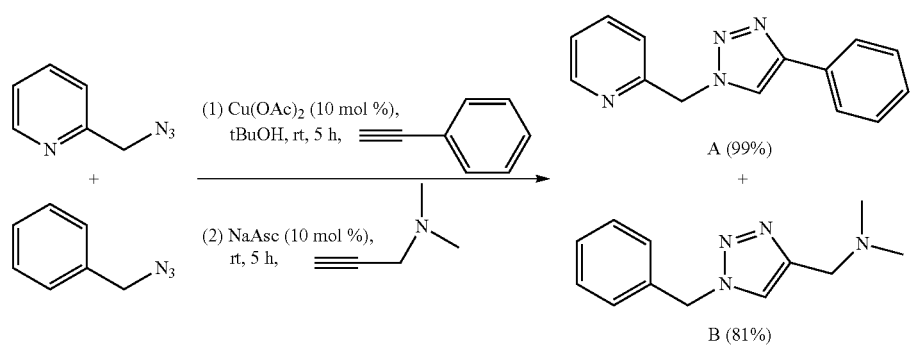

TABLE 2-continued

Azide Selectivity in CuAAC Reactions.

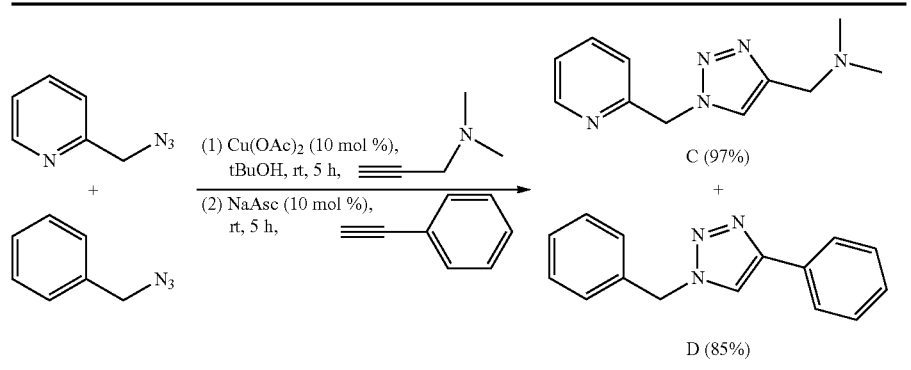

The chemoselectivity in organic azides (chelating vs non-chelating) opens up an opportunity to introduce two azido groups with inherently different reactivities into one substrate. The substrate may have the following general structures:

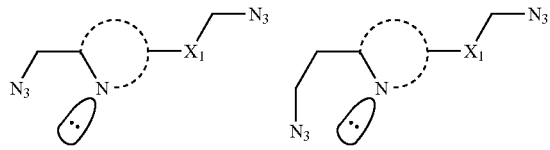

wherein:

The dashed circle represents a structural entity that supports a Lewis basic nitrogen atom (shown with a pair of electrons) and links two azido groups; and $X_1$ represents an aliphatic linking moiety or a direct link to the structural support entity.

In some embodiments, the substrate may have the following general structures:

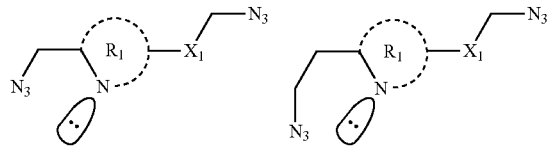

wherein:

The dashed circle around $R_1$ represents a ring structural group that supports a Lewis basic nitrogen atom (shown with a pair of electrons) and links two azido groups; and $X_1$ represents an aliphatic linking moiety or a direct link to the ring structural group.

In the above general structures, the chelating azide comprises the azide located in close proximity to the Lewis basic nitrogen on the structural support entity (left hand side of the formula), while the non-chelating azide is further from the Lewis basic nitrogen on the structural support entity linking moiety (right hand side of the formula). In general, the chelating azide may be located in a gamma or delta position relative to the Lewis base nitrogen atom of the structural support entity. The non-chelating azide is located more remotely (e.g., epsilon position or even more remotely) than the chelating azide relative to the Lewis base nitrogen atom. The structural support entity may comprise any functional group capable of providing a bias to the two attached azido groups so that one azido group is chelating, i.e., generally in the gamma or delta position, and the other azido group is non-chelating, i.e., in a position more remote than the chelating azide, e.g., epsilon or more remote. The close proximity of the chelating azide to the Lewis base nitrogen atom enables selective addition of a first alkyne moiety to the chelating azide followed sequentially by addition of a second alkyne moiety to the non-chelating azide. Selective reaction of the first alkyne with the bis-azide compound means that greater than 50% of the first alkyne couples with the chelating azide and less than 50% of the first alkyne couples with the non-chelating azide in the first addition reaction. More preferably, the selective reaction means that greater than 80% of the first alkyne couples with the chelating azide, greater than 90% of the first alkyne couples with the chelating azide, greater than 95% of the first alkyne couples with the chelating azide, or even greater than 99% of the first alkyne couples with the chelating azide.

In some embodiments, the structural support entity, the dashed circle, may comprise a five-membered ring, a six-membered ring, a seven-membered ring, or even an eight-membered ring, or higher, with five-membered and six-membered rings being preferred. In some embodiments, the structural support entity may be a cycloaliphatic linking moiety or an aromatic linking moiety. In some embodiments, the aromatic linking moiety may comprise a single aromatic ring or may comprises a fused ring system comprising two or more, such as two, three, or four, fused ring, in which each ring comprises a five-membered ring, a six-membered ring, a seven-membered ring, or even an eight-membered ring, or higher, with five-membered and six-membered rings being preferred. The aromatic linking moiety, whether it is a single ring or a fused ring system, may comprise heteroatoms in addition to the nitrogen atom shown in the general structure. These heteroatoms include nitrogen, sulfur, and oxygen.

Aromatic linking moieties may include pyridine, pyrimidine, pyrazine, pyridazine, triazines, pyrrole, pyrazole, imidazole, triazoles, quinoline, isoquinoline, cinnoline, quinazoline, quinoxaline, naphthyridines, indole, indazoles, benzoimidazole, benzotriazoles, pyrrolopyridines, pyrazolopyridines, imidazopyridines, triazolopyridines, pyrrolopyridazines, pyrazolopyridazines, imidazopyridazines, triazolopyridazines, pyrrolopyrimidines, pyrazolopyrimidines, purines, triazolopyrimidines, pyrrolopyrazines, pyrazolopyrazines, imidazopyrazines, triazolopyrazines, and so on.

In some embodiments, the $X_1$ aliphatic linking moiety comprises a direct bond between the methylene attached to the non-chelating azido group as shown in the formula or from one to 12 carbon atoms, such as from one to 6 carbon atoms, or from 1 to 4 carbon atoms. For example, the aliphatic linking moiety may comprise methylene, ethylene, propylenes (n-propylene, isopropylene), butylenes (n-butylene, isobutylene, tert-butylene), pentylenes (n-pentylene, isopentylene, neopentylene), hexylenes, and so on. The aliphatic linking moiety may comprise heteroatoms, including nitrogen, sulfur, oxygen, silicon, phosphorus, and selenium. Accordingly, linking moieties may comprise ethers such as dimethyl ether, diethyl ether, dipropyl ethers, dibutyl ethers, methylethyl ether, methyl propyl ethers, methyl butyl ethers, methyl pentyl ethers, and the like. The linking moieties may comprise thioethers, such as dimethylsulfane, ethyl(methyl) sulfane, diethylsulfane, dipropylsulfanes, dibutylsulfanes, methyl(propyl)sulfanes, ethyl(propyl)sulfanes, butyl(methyl)sulfanes, and the like.

Specific chemoselective azide substrates are depicted below in Table 3, which certain compounds labeled 4-7. These bisazides allow for sequential CuAAC reactions with two distinct alkynes in a one-pot procedure, without a protection/deprotection cycle. Moreover, it was shown previously that different alkynes have various reactivities to chelating azides, which makes it possible to obtain a single product by simply mixing two alkynes and a bisazide together in one experimental sequence. See Kuang, G.-C.; Guha, P. M.; Brotherton, W. S.; Simmons, J. T.; Stankee, L. A.; Nguyen, B. T.; Clark, R. J.; Zhu, L. *J. Am. Chem. Soc.* 2011, 133, 13984.

TABLE 3

| Unsymmetrical Bisazides | |
|---|---|
| Compound Name | Compound Structure |
| 2-((4-azido-butoxy)methyl)-6-(azidomethyl)-pyridine | 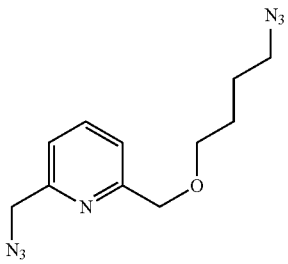<br>4 |
| 1-(4-azidobutyl)-4-(azidomethyl)-1H-1,2,3-triazole | 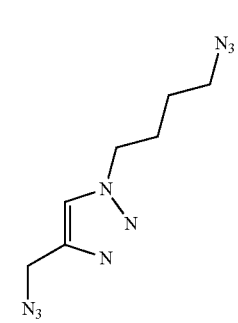<br>5 |

TABLE 3-continued

| Unsymmetrical Bisazides | |
|---|---|
| Compound Name | Compound Structure |
| 2,6-bis(azido-methyl)quinoline | 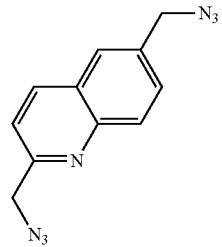<br>6 |
| 2,5-bis(azido-methyl)pyridine | 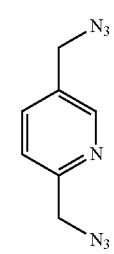<br>7 |
| 2,3-bis(azido-methyl)pyridine | 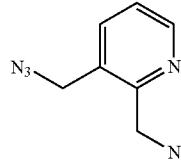 |
| 2,4-bis(azido-methyl)pyridine | 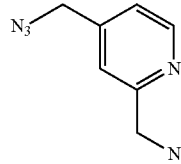 |
| 4-(4-azidobutyl)-1-(azidomethyl)-1H-1,2,3-triazole | 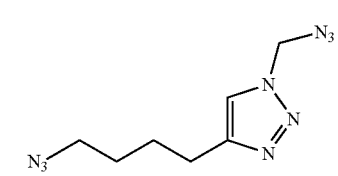 [SMILES: [N-]=[N+]=NCCCCc1cn(CN=[N+]=[N-])nn1] |
| 2-(azidomethyl)-5-(4-(azido-methyl)-phenyl)pyridine | 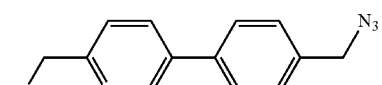 |
| 2,7-bis(azido-methyl)quinoline | 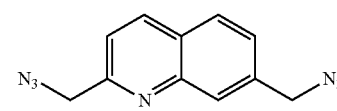 |
| 2,5-bis(azido-methyl)quinoline | 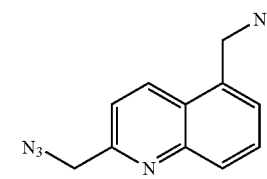 |

TABLE 3-continued

Unsymmetrical Bisazides

| Compound Name | Compound Structure |
|---|---|
| 2,6-bis(azido-methyl)-1H-benzo[d]-imidazole | 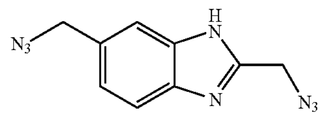 [SMILES: [N-]=[N+]=NCc1ccc2nc(CN=[N+]=[N-])[nH]c2c1] |
| 2,5-bis(azido-methyl)-1H-benzo[d]-imidazole | 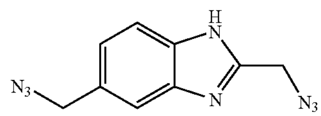 [SMILES: [N-]=[N+]=NCc1ccc2[nH]c(CN=[N+]=[N-])nc2c1] |
| 7-(4-azidobutyl)-6-(azidomethyl)-7H-purine | 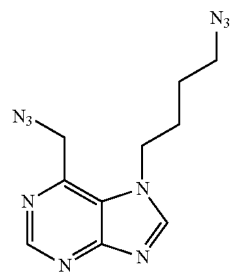 [SMILES: [N-]=[N+]=NCCCCn1cnc2ncnc(CN=[N+]=[N-])c21] |
| 7-(4-azidobutyl)-2-(azidomethyl)-7H-purine | 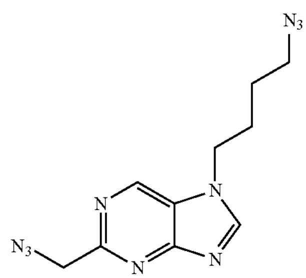 [SMILES: [N-]=[N+]=NCCCCn1cnc2nc(CN=[N+]=[N-])ncc21] |
| 8-(4-azidobutyl)-2-(azidomethyl)-7H-purine | 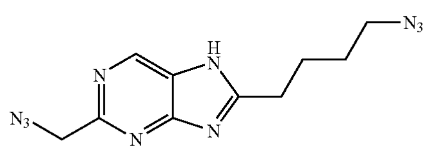 [SMILES: [N-]=[N+]=NCCCCc1nc2nc(CN=[N+]=[N-])ncc2[nH]1] |
| 8-(4-azidobutyl)-6-(azidomethyl)-7H-purine | 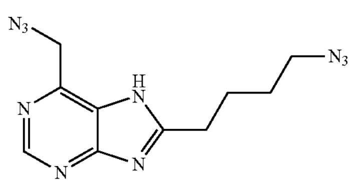 [SMILES: [N-]=[N+]=NCCCCc1nc2ncnc(CN=[N+]=[N-])c2[nH]1] |

The syntheses of unsymmetrical bisazides 4-7 containing chelating and non-chelating azido groups are shown in the Examples. Bisazides 4 and 7 contain a 2-(azidomethyl)pyridyl chelating component, and an aliphatic and a benzylic non-chelating azide, respectively. In bisazide 5, the N3 nitrogen atom on the triazolyl ring and the C4-azidomethyl group constitute a chelating component, while a non-chelating aliphatic azido group is attached via a 4-carbon linker. Compound 6 has a quinoline core with a chelating 2-azidomethyl and a non-chelating 6-azidomethyl groups. In 4-7, the chelating azido group would react with an alkyne molecule first under the $Cu(OAc)_2$-accelerated conditions, leaving the non-chelating azido group for the CuAAC reaction with the second alkyne under more strongly reducing conditions. See Kuang, G.-C.; Guha, P. M.; Brotherton, W. S.; Simmons, J. T.; Stankee, L. A.; Nguyen, B. T.; Clark, R. J.; Zhu, L. *J. Am. Chem. Soc.* 2011, 133, 13984.

The single crystal structure of complex $[Cu_2(7)_2Cl_4]$ (see FIG. 1) reveals the selective azido-copper interaction in bisazide 7, which is the source of its chemoselectivity in CuAAC reactions. The copper(II) center is square pyramidal, where the bidentate chelating 2-(azidomethyl)pyridyl moiety and two chloride ions constitute the square plane. The non-chelating azido group is left unbound.

According to the method of the present invention, the above-described bisazides are sequentially reacted with two alkynes, which may be the same or different, in a single pot synthesis. An alkyne for reaction according to the method of the present invention may have the general structure:

wherein $Y_1$ represents a functional group. The functional group may be linked directly to the alkyne moiety or may be bonded to the alkyne moiety by an aliphatic linking group or an aromatic linking group.

In some embodiments, the functional group may comprise an aromatic linking moiety. The aromatic linking moiety may comprise a five-membered ring or a six-membered ring, or five-membered and six-membered fused ring systems. In some embodiments, the aromatic linking moiety may comprise a fused ring system comprising two or more, such as two, three, or four, fused ring, in which each ring comprises a five-membered ring, a six-membered ring, or a combination of a five-membered and six-membered ring. The aromatic linking moiety, whether it is a single ring or a fused ring system, may comprise heteroatoms. These heteroatoms include nitrogen, sulfur, phosphorus, selenium, and oxygen.

Aromatic linking moieties may include benzene, naphthalene, phenanthrene, anthracene, pyrene, tetracene, pyridine, pyrimidine, pyrazine, pyridazine, triazines, pyrrole, imidazole, triazoles, quinoline, cinnoline, quinazoline, quinoxaline, naphthyridines, indole, indazoles, benzoimidazole, benzotriazoles, purines, furan, benzofuran, thiophene, benzothiophene, and so on.

In some embodiments, the functional group may comprise an aliphatic linking moiety. The aliphatic linking moiety may comprise from one to 12 carbon atoms, such as from one to 6 carbon atoms, or from 1 to 4 carbon atoms. The aliphatic linking moiety may comprise heteroatoms, including nitrogen, sulfur, oxygen, silicon, phosphorus, and selenium.

Functional groups include nitro, hydroxyl, alkyl having from 1 to four carbon atoms, alkenyl, phenyl, benzyl, fluoro, chloro, bromo, iodo, carbonyl, aldehyde, haloformyl, carboxyl, carboxylate, ester, ether, amide, amine, azo, cyano, sulfanyl, sulfinyl, and sulfonyl.

The $Y_1$ group may comprise macromolecular functionality. Macromolecular functionality includes hydrocarbon polymers such as polyethylene and polypropylene, heteroaromatic polymers such as polyesters, polyamides, and polyurethanes and biological macromolecules such as peptides, proteins, nucleic acid polymers such as DNA and RNA, and polysaccharides.

The alkynes for reaction with the bisazide may be the same or different. Advantageously, the method of the present invention enables chemoselective sequential reaction of two different alkynes onto a bisazide in a single pot reaction. The reaction may proceed without the need for protection/deprotection of reactive functional groups.

According to the method of the present invention, a bisazide compound and a first alkyne (labeled (a) in the reaction sequences (1) through (3) below) are contacted in the presence of a catalyst, which catalyzes the reaction of the first alkyne with the chelating azide (as shown above, the azide in close proximity, e.g., gamma or delta, relative to the Lewis base nitrogen atom), thereby linking the first alkyne by the formation of a triazole ring. The bisazide and first alkyne are contacted in a molar ratio ranging from about 0.8:1 to about 1.2:1, preferably about 1:1. Catalysts for this first reaction include Cu(II) ion. A suitable source of Cu(II) ion is copper (II) acetate. The catalyst concentration may range from about 5% to about 20% of the concentration of the first alkyne, preferably about 10% of the concentration of the first alkyne.

Thereafter, the resultant mono-azide is contacted with a second alkyne (labeled (b) in the reaction sequences (1) through (3) below), which optionally occurs without isolating the mono-azide intermediate, and a suitable amount of catalyst. This contact links the second alkyne to the mono-azide by the formation of a second triazole ring. The bisazide and the second alkyne are contacted in a molar ratio ranging from about 0.8:1 to about 1.2:1, preferably about 1:1. Catalysts for this second reaction include Cu(I) ion. Suitable sources of Cu(I) ion include CuI, CuBr, CuCl, copper(I) acetate, and so on. The Cu(I) ion may be generated in situ by the addition of a Cu(II) source and a sufficient concentration of antioxidant to reduce the Cu(II) ions to Cu(I) ions. Suitable antioxidants include ascorbic acid, sodium sulfite, and triaryl or trialkyl phosphine. In general, the concentration of the antioxidant should be at least 100% of the concentration of the added Cu(II) ion concentration, preferably at least 150%, such as about 200% of the concentration of the added Cu(II) ion concentration. The catalyst concentration may range from about 5% to about 20% of the concentration of the alkyne, preferably about 10% of the concentration of the alkyne.

In one specific embodiment, 1-ethynyl-4-nitrobenzene and propargyl alcohol were employed as alkyne substrates in demonstrating the chemoselective double-click reaction involving bisazides 4-7 (Reaction Sequence (1)). The addition of the first alkyne to a solution of a bisazide in a 1:1 molar ratio in the presence of 10 mol % Cu(OAc)$_2$ resulted in the formation of mono-triazoles T1-T8 (See Tables 4A and 4B). The high isolated yields (entries 1-8) indicated that the structures of bisazides and alkynes had only a marginal influence on the efficiency and chemoselectivity of the first CuAAC reaction.

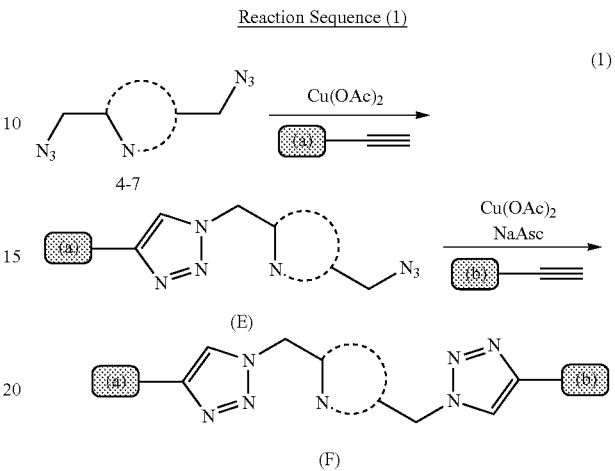

Addition of the second alkyne with a catalytic amount of Cu(OAc)$_2$ (10 mol %) and sodium ascorbate (20 mol %) to the CH$_2$Cl$_2$/CH$_3$OH solution of the purified monotriazole products resulted in the formation of bistriazoles TT1-TT8 in good yields (yield of F). The results shown in Table 4 from the two-step sequence demonstrate the high reactivity of the chelating azide, which undergoes the Cu(OAc)$_2$-mediated cycloaddition with an alkyne without affecting the non-chelating azide. The addition of sodium ascorbate affords a high concentration of copper(I), which is apparently needed for the non-chelating azido group to ligate with the second alkyne. Thus, by using appropriate reagents, sequential chemoselective ligation of unsymmetrical bisazides 4-7, each of which contains a chelating and non-chelating azido groups, is achieved.

TABLE 4A

Chemoselective formation of monotriazoles (Yield of E of Reaction Sequences (1) or (2)).[a]

| entry | azide | monotriazole (E) | yield of E[b] |
|---|---|---|---|
| 1 | 4 | T1 | 93% |
| 2 | 4 | T2 | 84% |
| 3 | 5 | T3 | 82% |

TABLE 4A-continued

Chemoselective formation of monotriazoles (Yield of E of Reaction Sequences (1) or (2)).[a]

| entry | azide | monotriazole (E) | yield of E[b] |
|---|---|---|---|
| 4 | 5 | T4 | 82% |
| 5 | 6 | T5 | 90% |
| 6 | 6 | T6 | 88%[c] |
| 7 | 7 | T7 | 99% |
| 8 | 7 | T8 | 87% |
| 9[d] | 7 | T7 | 90% |
| 10[d] | 7 | T8 | 89% |

[a] Azide (0.1 mmol) and alkyne (0.1 mmol) with 10 mol % of Cu(OAc)$_2$ at rt; entries 1-8 in CH$_3$OH/CH$_2$Cl$_2$ (1:1 v/v, 0.5 mL);
[b] Isolated yield after purification by column chromatography;
[c] 2-3% impurity is contained in the isolated product, presumably the reverse regioisomer and/or homobistriazole(s);
[d] HEPES buffer (0.5 mL, 0.5M, pH 7.0).

TABLE 4B

Chemoselective formation of monotriazoles (Yield of F or G of Reaction Sequences (1) or (2)).[a]

| entry | azide | bistriazole (F or G) | yield of F[b] | yield of G[b] |
|---|---|---|---|---|
| 1 | 4 | TT1 | 87% | 97% |
| 2 | 4 | TT2 | 91% | 95% |
| 3 | 5 | TT3 | 74% | 78% |
| 4 | 5 | TT4 | 69% | 74% |
| 5 | 6 | TT5 | 81% | 87% |
| 6 | 6 | TT6 | 77%[c] | 84%[c] |
| 7 | 7 | TT7 | 80% | 92% |
| 8 | 7 | TT8 | 76% | 88% |

TABLE 4B-continued

Chemoselective formation of monotriazoles (Yield of F or G of Reaction Sequences (1) or (2)).[a]

| entry | azide | bistriazole (F or G) | yield of F[b] | yield of G[b] |
|---|---|---|---|---|
| 9[d] | 7 | TT7 | 75% | 85% |
| 10[d] | 7 | TT8 | 73% | 82% |

[a]Azide (0.1 mmol) and alkyne (0.1 mmol) with 10 mol % of Cu(OAc)$_2$ at rt; entries 1-8 in CH$_3$OH/CH$_2$Cl$_2$ (1:1 v/v, 0.5 mL);
[b]Isolated yield after purification by column chromatography;
[c]2-3% impurity is contained in the isolated product, presumably the reverse regioisomer and/or homobistriazole(s);
[d]HEPES buffer (0.5 mL, 0.5M, pH 7.0).

In addition to the stepwise syntheses of mono- and bistriazoles, a "one-pot" double-click ligation experiment was carried out without the isolation of the monotriazole intermediate (Reaction Sequence (2)). Five hours after the introduction of the first alkyne into the CH$_2$Cl$_2$/CH$_3$OH solution of a bisazide in the presence of 10 mol % Cu(OAc)$_2$, the second alkyne was added, which was accompanied by a sodium ascorbate solution to reduce Cu(OAc)$_2$. The CuAAC reaction between the non-chelating azide and the second alkyne proceeded to afford single detectable bistriazole products in excellent yields (Table 4B, yield of G). It is notable that the order of alkyne addition, not the identity of the alkyne, directs the double-click reaction to reach different bistriazole products. Comparing to the overall isolated yields of bistriazoles from the stepwise procedure (Table 4B, yield of F), the higher yields of the one-pot procedure (yield of G) suggests that not only the chemoselectivity of the double-click reaction is maintained, but efficient isolation of products with minimal material loss is managed without separating the monotriazole intermediate.

Reaction Sequence (2)

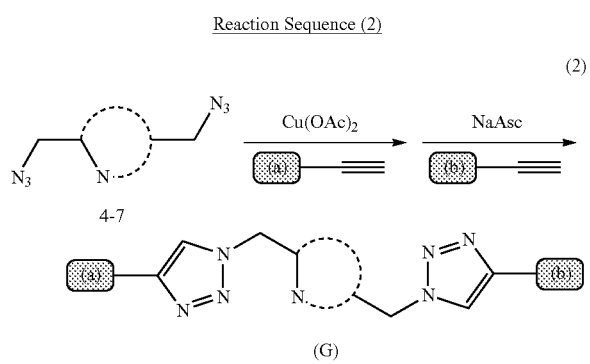

The bistriazole products from both stepwise (Table 4B, entries 9 and 10) and one-pot procedures were obtained in good isolated yields, which lends promise in bioconjugation applications. See Kalia, J.; Raines, R. T. Curr. Org. Chem. 2010, 14, 138.

It was previously disclosed that reactivities of various alkynes differ under Cu(OAc)$_2$-mediated conditions. See Kuang, G.-C.; Guha, P. M.; Brotherton, W. S.; Simmons, J. T.; Stankee, L. A.; Nguyen, B. T.; Clark, R. J.; Zhu, L. J. Am. Chem. Soc. 2011, 133, 13984. For example, enhanced acidity of an alkyne leads to increased rate of the CuAAC reaction, because alkyne deprotonation was shown to be kinetically significant. See Kuang et al. The differences in reactivities of both alkynes and azides make it possible to perform chemoselective three-component (two alkynes with different reactivities and a bisazide) reactions.

In the three-component reaction involving two different alkynes and bisazide 7 (Reaction Sequence (3)), the alkyne with a higher reactivity (e.g. 1-ethynyl-4-nitrobenzene and 4-ethynyltoluene) shall undergo Cu(OAc)$_2$-mediated CuAAC reaction selectively with the chelating azido group of 7. After the first reaction is completed, the addition of sodium ascorbate to the reaction mixture would lead to the second CuAAC reaction between the non-chelating azido group and the less reactive alkyne (e.g. propargyl alcohol and 1-hexyne).

Reaction Sequence (3)

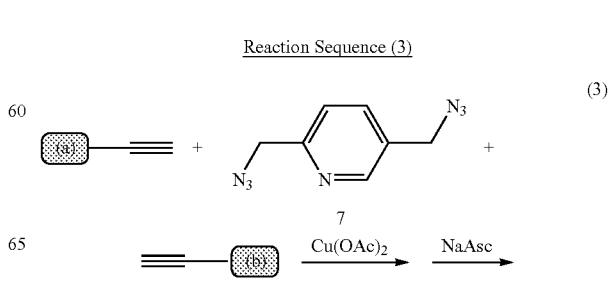

One important benefit of the CuAAC reaction for applications in chemical biology and material science is the undiminished reactivity under physiological conditions. Bisazide 7 was chosen to test the viability of chemoselective double ligation in an aqueous solution buffered by HEPES at pH 7.

-continued

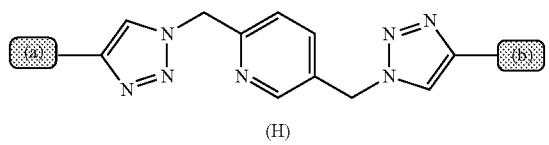

(H)

In agreement with the above expectation, the inclusion of two alkynes (1-ethynyl-4-nitrobenzene and propargyl alcohol) with bisazide 7 in CH$_3$CN resulted in the first cycloaddition selectively between the chelating azido group and 1-ethynyl-4-nitrobenzene, and the second CuAAC reaction between the non-chelating azido and propargyl alcohol to afford the bistriazole in 70% isolated yield (Table 5, entry 1). Compared to propargyl alcohol, 1-hexyne has a lower reactivity in CuAAC reaction. The large disparity between the reactivities of 1-ethynyl-4-nitrobenzene and 1-hexyne manifested in the one-pot synthesis of bistriazole TT9, which was obtained in an almost quantitative yield (Table 5, entry 2). The one-pot reaction of entry 2 was monitored via $^1$H NMR spectroscopy, from which the exclusive ligation between the chelating azido group and 1-ethynyl-4-nitrobenzene was observed in CD$_3$CN in the presence of the idle 1-hexyne. The second CuAAC reaction after the addition of sodium ascorbate did not take place at the prescribed concentration levels in the NMR tube, even at an elevated temperature.

TABLE 5

One-pot, three-component reactions according to Reaction Sequence (3).[a]

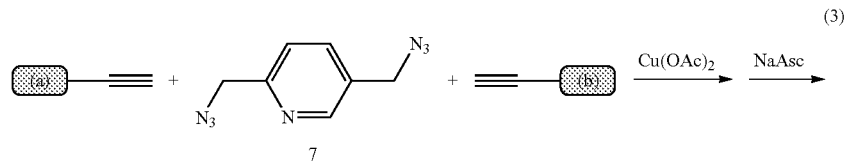

(3)

(H)

| entry | bistriazole (H) | yield of H[b] |
|---|---|---|
| 1 | TT7 | 70% |
| 2 | TT9 | 98% |
| 3 | TT10 | 74%[c] |

[a]Bisazide 7 (0.1 mmol) and two alkynes (0.1 mmol) in CH$_3$CN (0.5 mL) with addition of Cu(OAc)$_2$ (10 mol %) followed by adding NaAsc (20 mol %) after 5 h at rt.

[b]Isolated yield after purification by column chromatography.

[c]3% impurity is contained in the isolated product presumably the reverse regioisomer and/or homobistriazole(s).

4-Ethynyltoluene and 1-hexyne are also effective in the one-pot double-click reaction involving bisazide 7, in which the aromatic 4-ethynyltoluene and the aliphatic 1-hexyne were consumed sequentially to afford bistriazole TT10. The methyl groups of the two alkynes could conceivably be replaced by other structural entities, thus offering an attractive tool for the selective conjugation of multiple components under mild conditions.

In conclusion, a method for the one-pot chemoselective double-click reaction of three components is described. This strategy employs unsymmetrical bisazides containing chelating and non-chelating azido groups, which exhibit different reactivities in CuAAC reactions. The easy preparation and simple structures of bisazides 4-7 suggest that they can be used as convenient conjugation linkers to join two ethynyl-functionalized building blocks with high regioselectivity under mild, including physiological conditions. Exploring the utilities of the bisazide linkers in areas of bioconjugation and material sciences is an ongoing effort in our laboratory.

Having described the invention in detail, it will be apparent that modifications and variations are possible without departing from the scope of the invention defined in the appended claims.

EXAMPLES

The following non-limiting examples are provided to further illustrate the present invention.

1. Materials and General Methods

Reagents and solvents were purchased from various commercial sources and used without further purification unless otherwise stated. The purity of $Cu(OAc)_2$ is over 99.0%. Analytical thin-layer chromatography (TLC) was performed using TLC plates pre-coated with silica gel 60 F254. Flash column chromatography was performed using 40-63 μm (230-400 mesh ASTM) silica gel as the stationary phase. Silica gel was flame-dried under reduced pressure to remove adsorbed moisture before use. $^1H$ NMR spectra were recorded at 300 or 500 MHz, and $^{13}C$ NMR spectra were collected at 75 MHz or 125 MHz. All chemical shifts were reported in δ units relative to tetramethylsilane.

2. Syntheses and Characterizations of New Compounds 2.1 Syntheses and Characterizations of Bisazides 4-7

Example 1

Synthesis of Compound 4

Compound 4 may be prepared by the following sequence of reactions:

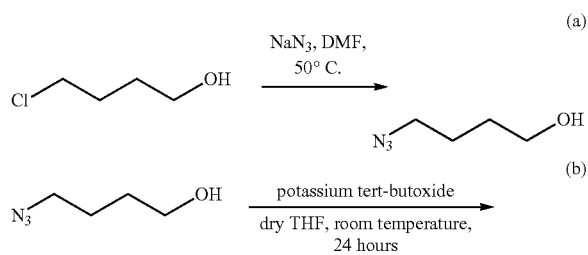

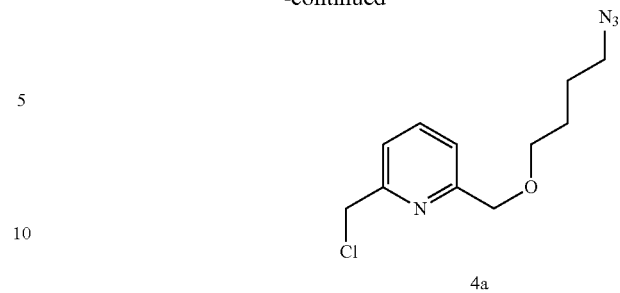

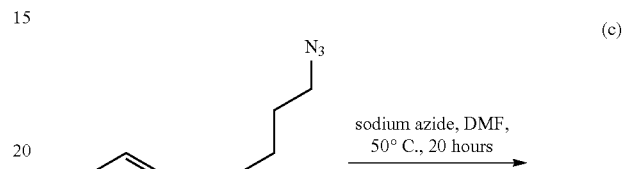

The yield is 21% for three steps.

Example 1A 4-azidobutan-1-ol

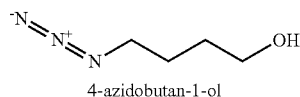

4-azidobutan-1-ol

4-Chlorobutanol (0.46 mL, 4.6 mmol) was dissolved in DMF (10 mL), followed by the addition of $NaN_3$ (0.75 g, 12 mmol). The solution was stirred overnight at 50° C. before cooling down to rt. EtOAc (50 mL) was added into the reaction mixture, and the white precipitate was removed by filtration. The solution was washed with $H_2O$ (30 mL) and saturated $NH_4Cl$ solution (3×30 mL) sequentially. The organic portion was dried over anhydrous $Na_2SO_4$ before solvent was evaporated under reduced pressure to give the crude product, which was used directly in the next reaction without purification.

Example 1B

2-((-4-azidobutoxy)methyl)-6-(chloromethyl)pyridine

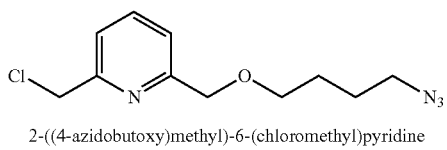

2-((4-azidobutoxy)methyl)-6-(chloromethyl)pyridine

The crude 4-azidobutanol was dissolved in dry THF (10 mL). 2,6-Bis(chloromethyl)pyridine (0.81 g, 4.6 mmol) and potassium tert-butoxide (1.04 g, 9.2 mmol) were added sequentially. The solution was stirred overnight at rt before solvent was evaporated under reduced pressure to afford crude 4a. The crude product was used directly in the next reaction without isolation.

Example 1C

2-((4-azidobutoxy)methyl)-6-(azidomethyl)pyridine

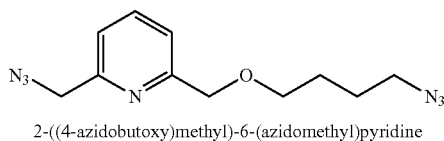

2-((4-azidobutoxy)methyl)-6-(azidomethyl)pyridine

The crude compound 4a was dissolved in DMF (10 mL) followed by the addition of $NaN_3$ (0.75 g, 12 mmol). The solution was heated to 50° C. and stirred overnight before cooling down to rt. EtOAc (25 mL) was added into the reaction mixture, and the white precipitate was removed by filtration. The solution was washed with a saturated $NH_4Cl$ solution (4×20 mL). The organic portion was dried over anhydrous $Na_2SO_4$ before solvent was evaporated under reduced pressure. The crude product was purified using silica chromatography eluted with $CH_2Cl_2$ to afford compound 4 in an oil form (0.25 g, 21% overall yield of the three-step sequence). $^1H$ NMR (300 MHz, $CDCl_3$): δ/ppm 7.74 (t, J=7.7 Hz, 1H), 7.40 (d, J=7.6 Hz, 1H), 7.25 (d, J=8.4 Hz, 1H), 4.62 (s, 2H), 4.46 (s, 2H), 3.60 (s(b), 2H), 3.32 (s(b), 2H), 1.76-1.72 (m, 4H); $^{13}C$ NMR (75 MHz, $CDCl_3$): δ/ppm 159.0, 155.1, 137.7, 120.7, 120.5, 73.7, 70.5, 55.6, 51.4, 27.0, 25.9; HRMS ($ESI^+$): calcd. ($C_{11}H_{15}N_7O+H^+$) 262.1416, found 262.1414.

Example 2

Synthesis of Compound 5

Compound 5 may be prepared by the following sequence of reactions:

(a)

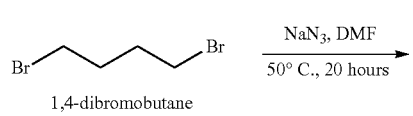

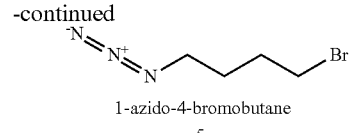

1-azido-4-bromobutane
5a

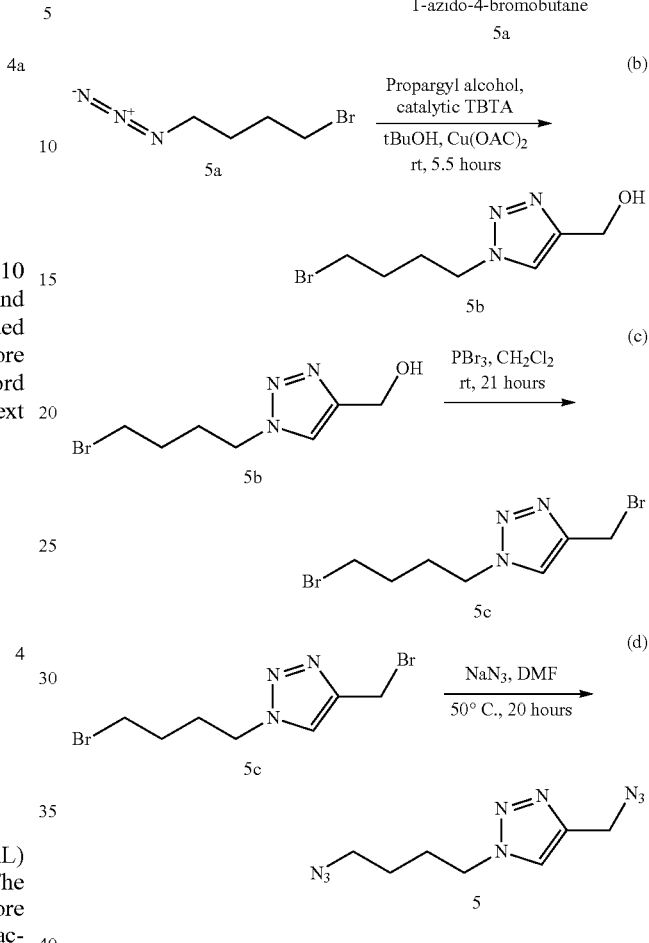

Example 2A

1-azido-4-bromobutane

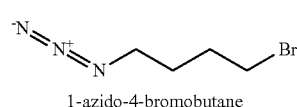

1-azido-4-bromobutane 1,4-Dibromobutane (6.46 g, 30 mmol), DMF (20 mL) and $NaN_3$ (0.97 g, 15 mmol) were added to a round-bottom flask sequentially. The solution was heated to 50° C. and stirred for 20 h before cooling to rt. EtOAc (50 mL) was added into the reaction mixture and the white precipitate was removed by filtration. The solution was washed with $H_2O$ (30 mL) and a saturated $NH_4Cl$ solution (3×30 mL) sequentially. The organic portion was dried over anhydrous $Na_2SO_4$ before solvent was evaporated under reduced pressure. The residue was chromatographed on silica gel using $CH_2Cl_2$ in hexanes (0-4%) to afford compound 5a (693 mg, 26%). $^1H$ NMR (300 MHz, $CDCl_3$): δ/ppm 3.44 (t, J=6.5 Hz, 2H), 3.34 (t, J=6.7

Hz, 2H), 2.01-1.91 (m, 2H), 1.81-1.72 (m, 2H); $^{13}$C NMR (75 MHz, CDCl$_3$): δ/ppm 50.7, 33.0, 29.9, 27.6.[1]

Example 2B (1-(4-bromobutyl)-1H-1,2,3-triazol-4-yl)methanol

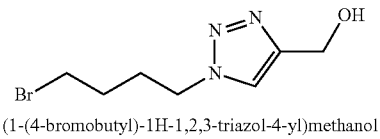

(1-(4-bromobutyl)-1H-1,2,3-triazol-4-yl)methanol

Compound 5a (430.7 mg, 2.42 mmol), propargyl alcohol (141.3 mg, 2.52 mmol), tBuOH (0.7 mL), TBTA (2.9 mg, 5.4 μmol) and Cu(OAc)$_2$ (50 μL, 0.4 M in H$_2$O, 10 μmol) were added to a vial and stirred at rt for 5.5 h before being diluted with CH$_2$Cl$_2$. The crude product was chromatographed on silica gel and the solution was concentrated under reduced pressure to yield compound 5b in an oil form (514.1 mg, 91%). $^1$H NMR (300 MHz, CDCl$_3$): δ/ppm 7.55 (s, 1H), 4.78 (d, J=5.9 Hz, 2H), 4.38 (t, J=7.0 Hz, 2H), 3.40 (t, J=6.4 Hz, 2H), 3.20 (s, 1H), 2.13-2.03 (m, 2H), 1.94-1.82 (m, 2H); $^{13}$C NMR (75 MHz, CDCl$_3$): δ/ppm 148.0, 122.0, 55.8, 49.3, 32.6, 29.2, 28.7; HRMS (ESL): calcd. (C$_7$H$_{12}$BrN$_3$O+H$^+$) 234.0242, found 234.0229.

Example 2C 1-(4-bromobutyl)-4-(bromomethyl)-1H-1,2,3-triazole

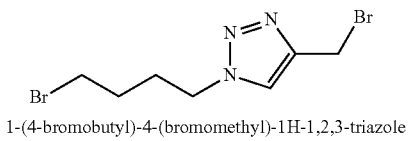

1-(4-bromobutyl)-4-(bromomethyl)-1H-1,2,3-triazole

Crude compound 5b (514.1 mg, 2.20 mmol) from the previous step was dissolved in dry CH$_2$Cl$_2$ (3 mL), followed by the dropwise addition of a PBr$_3$ solution in CH$_2$Cl$_2$ (1 M, 2.5 mL) at 0° C. The solution was stirred at rt for 19 h before a NaHCO$_3$ solution (20 mL, 0.1 M in H$_2$O) was added. The organic layer was partitioned and dried over anhydrous Na$_2$SO$_4$. The product was concentrated under reduced pressure to yield compound 5c in an oil form (347.6 mg, 53%). $^1$H NMR (300 MHz, CDCl$_3$): δ/ppm 7.68 (s, 1H), 4.61 (s, 2H), 4.43 (t, J=7.0 Hz, 2H), 3.43 (t, J=6.3 Hz, 2H), 2.17-2.07 (m, 2H), 1.94-1.85 (m, 2H); $^{13}$C NMR (75 MHz, CDCl$_3$): δ/ppm 144.0, 123.7, 50.0, 32.5, 29.2, 28.6, 20.8; HRMS (ESI$^+$): calcd. (C$_7$H$_{11}$Br$_2$N$_3$+H$^+$) 295.9398 found 295.9416.

Example 2D 1-(4-azidobutyl)-4-(azidomethyl)-1H-1,2,3-triazole

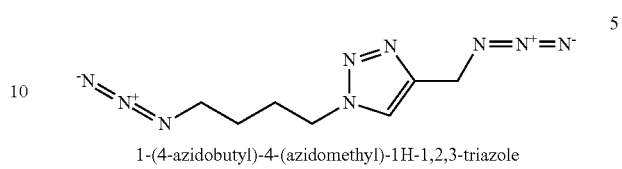

1-(4-azidobutyl)-4-(azidomethyl)-1H-1,2,3-triazole

Compound 5c (347.6 mg, 1.17 mmol) was dissolved in DMF (10 mL), followed by the addition of NaN$_3$ (341.2 mg, 5.25 mmol). The solution was heated to 50° C. and stirred overnight before cooling down to rt. EtOAc (50 mL) was added into the reaction mixture and the white precipitate was removed by filtration. The solution was washed with a saturated NH$_4$Cl solution (3×40 mL). The organic portion was dried over anhydrous Na$_2$SO$_4$ before solvent was evaporated under vacuum to afford compound 5 in an oil form (187.0 mg, 72%). $^1$H NMR (300 MHz, CDCl$_3$): δ/ppm 7.56 (s, 1H), 4.50 (s, 2H), 4.42 (t, J=7.0 Hz, 2H), 3.35 (t, J=6.5 Hz, 2H), 2.08-1.98 (m, 2H), 1.68-1.56 (m, 2H); $^{13}$C NMR (75 MHz, CDCl$_3$): δ/ppm 142.3, 122.3, 50.5, 49.6, 45.4, 27.3, 25.6; HRMS (ESI$^+$): calcd. (C$_7$H$_{11}$N$_9$+Na$^+$) 244.1035 found 244.1043.

Example 3

Synthesis of Compound 6

Compound 6 may be prepared by the following sequence of reactions:

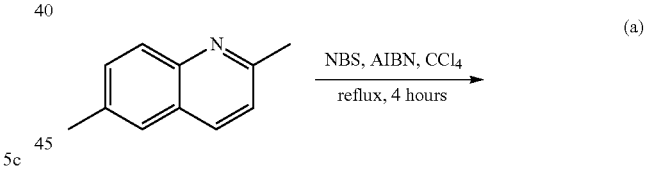

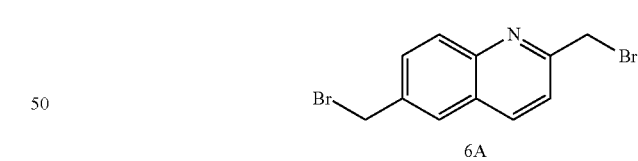

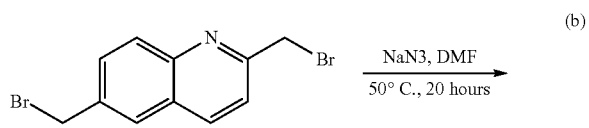

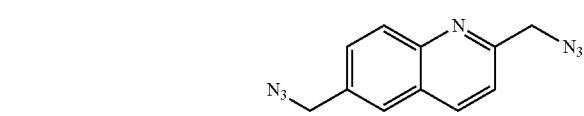

Example 3A 2,6-bis(bromomethyl)quinoline

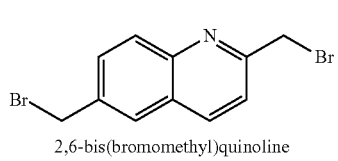

2,6-bis(bromomethyl)quinoline 2,6-Dimethylquinoline (1.00 g, 6.40 mmol) was dissolved in CCl$_4$ (50 mL). NBS (2.38 g, 13.4 mmol) and AIBN (41.9 mg, 0.25 mmol) were added sequentially under argon protection. The solution was heated to reflux for 4 h before cooling to rt. The precipitate was filtered and the solvent was evaporated under reduced pressure. The residue was chromatographed on silica gel using CH$_2$Cl$_2$ to afford compound 6a (0.54 g, 27%). $^1$H NMR (300 MHz, CDCl$_3$): δ/ppm 8.15 (d, J=8.5 Hz, 1H), 8.05 (d, J=8.7 Hz, 1H), 7.81 (s, 1H), 7.75 (dd, J=2.0, 8.7 Hz, 1H), 7.58 (d, J=8.5 Hz, 1H), 4.70 (s, 2H), 4.66 (s, 2H); $^{13}$C NMR (75 MHz, CDCl$_3$): δ/ppm 157.7, 147.3, 137.3, 136.7, 131.1, 130.2, 127.5, 127.2, 121.9, 34.3, 33.0.[2]

Example 3B 2,6-bis(azidomethyl)quinoline

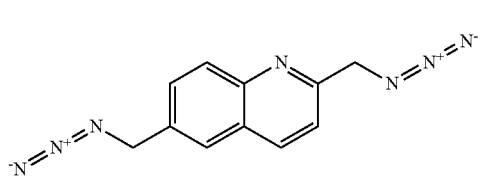

2,6-bis(azidomethyl)quinoline

Compound 6a (152.3 mg, 0.48 mmol) was dissolved in DMF (5.0 mL), followed by the addition of NaN$_3$ (402.6 mg, 6.2 mmol). The solution was heated to 50° C. and stirred for 5.5 h before cooling down to rt. EtOAc (50 mL) was added into the reaction mixture and the white precipitate was removed by filtration. The solution was washed with a saturated NH$_4$Cl solution (3×40 mL). The organic portion was dried over anhydrous Na$_2$SO$_4$ before solvent was evaporated under reduced pressure to afford compound 6 (98 mg, 85%). $^1$H NMR (300 MHz, CDCl$_3$): δ/ppm 8.20 (d, J=8.5 Hz, 1H), 8.10 (d, J=8.7 Hz, 1H), 7.78 (s, 1H), 7.68 (dd, J=1.9, 8.7 Hz, 1H), 7.50 (d, J=8.4 Hz, 1H), 4.68 (s, 2H), 4.56 (s, 2H); $^{13}$C NMR (75 MHz, CDCl$_3$): δ/ppm 156.5, 147.4, 137.2, 134.1, 130.0, 129.9, 127.3, 126.6, 120.2, 56.2, 54.6; m.p.: 55-57° C.; HRMS (ESI$^+$): calcd. (C$_{11}$H$_9$N$_7$+H$^+$) 240.0998 found 240.1016.

Example 4

Synthesis of Compound 7

Compound 7 may be prepared by the following sequence of reactions:

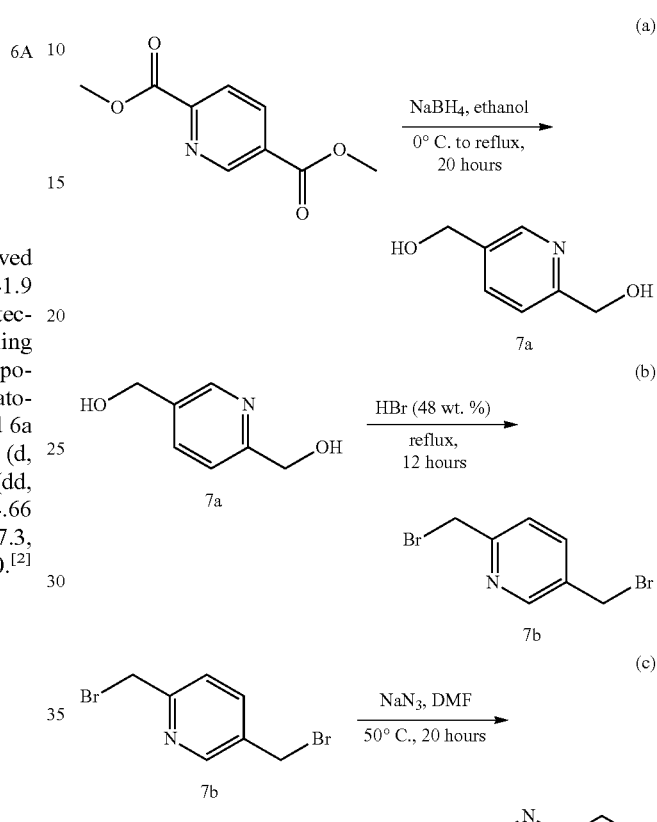

Example 4A

Pyridine-2,5-diyldimethanol

Pyridine-2,5-diyldimethanol 2,5-Bis(methoxycarbonyl)pyridine (1.06 g, 5.4 mmol) was suspended in ethanol (20 mL), and the mixture was cooled to 0° C. in an ice bath. NaBH$_4$ (0.82 g, 22 mmol) was added in small portions to the mixture. After the reaction mixture was stirred for 1 h at 0° C., the ice bath was removed. Stirring was continued for 3 h at rt, before the reaction mixture was heated overnight under reflux. After the reaction mixture was cooled to rt, the solvent was removed under reduced pressure. The residue was chromatographed on silica gel to afford compound 7a (0.62 g, 83%). $^1$H NMR (500 MHz, CDCl$_3$): δ/ppm 8.53 (s, 1H), 7.73 (d, J=7.9 Hz, 1H), 7.26 (d, J=7.9 Hz, 1H), 4.77 (s, 2H), 4.75 (s, 2H); $^{13}$C NMR (125 MHz, CDCl$_3$): δ/ppm 158.6, 147.5, 136.0, 135.0, 120.6, 64.3, 62.8.[3]

Example 4B 2,5-bis(bromomethyl)pyridine

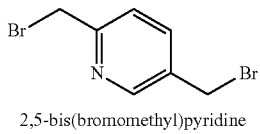

2,5-bis(bromomethyl)pyridine

A solution of 7a (0.62 g, 4.5 mmol) in 48 wt % HBr was heated overnight under reflux. After the reaction was cooled to rt, the mixture was poured onto ice and neutralized with aqueous NaOH (1 M). The resulting precipitate was collected and chromatographed on silica gel using CH$_2$Cl$_2$ to give 7b (0.74 g, 62%). $^1$H NMR (300 MHz, CDCl$_3$): δ/ppm 8.51 (s, 1H), 7.67 (d, J=10.0 Hz, 1H), 7.35 (d, J=10.0 Hz, 1H), 4.47 (s, 2H), 4.37 (s, 2H).[4]

Example 4C 2,5-bis(azidomethyl)pyridine

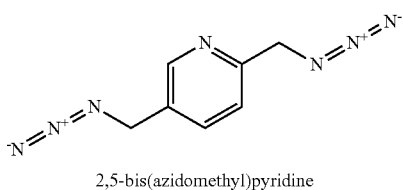

2,5-bis(azidomethyl)pyridine

Compound 7b (0.74 g, 2.8 mmol) was dissolved in DMF (10.0 mL), followed by the addition of NaN$_3$ (0.91 g, 14 mmol). The solution was heated to 50° C. and stirred overnight before cooling down to rt. EtOAc (50 mL) was added into the reaction mixture and the white precipitate was removed by filtration. The solution was washed with a saturated NH$_4$Cl solution (3×40 mL). The organic portion was dried over anhydrous Na$_2$SO$_4$ before solvent was evaporated under reduced pressure to afford compound 7 in an oil form (0.43 g, 81%). $^1$H NMR (300 MHz, CDCl$_3$): δ/ppm 8.55 (s, 1H), 7.71 (d, J=9.0 Hz, 1H), 7.39 (d, J=9.0 Hz, 1H), 4.51 (s, 2H), 4.41 (s, 2H); $^{13}$C NMR (75 MHz, CDCl$_3$): δ/ppm 156.1, 149.4, 137.0, 130.7, 122.2, 55.5, 52.0; HRMS (ESI$^+$): calcd. (C$_7$H$_7$N$_7$+H$^+$) 190.0841 found 190.0843.

Example 5

Preparation of Monotriazole T1

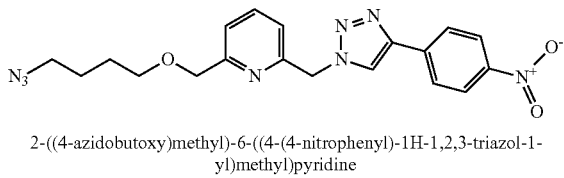

2-((4-azidobutoxy)methyl)-6-((4-(4-nitrophenyl)-1H-1,2,3-triazol-1-yl)methyl)pyridine The general procedure described in this Example 5 was used to prepare monotriazoles T2 through T8 in the following examples 6-11. Compound 4 (26.1 mg, 0.10 mmol) and 1-ethynyl-4-nitrobenzene (15.1 mg, 97%, 0.10 mmol) were dissolved in the mixed solvents of CH$_3$OH (0.25 mL) and CH$_2$Cl$_2$ (0.25 mL), or a HEPES buffer solution (0.5 mL, pH=7.0), followed by addition of a Cu(OAc)$_2$ solution (25 μL, 0.4 M in H$_2$O, 10 μmol). The reaction mixture was stirred at rt for 5 h before being diluted with CH$_2$Cl$_2$ and purified by silica column chromatography eluted by EtOAc/CH$_2$Cl$_2$ to yield compound T1 (37.5 mg, 92%). $^1$H NMR (300 MHz, CDCl$_3$): δ/ppm 8.27 (d, J=9.0 Hz, 2H), 8.10 (s, 1H), 8.00 (d, J=8.9 Hz, 2H), 7.73 (t, J=7.7 Hz, 1H), 7.44 (d, J=7.8 Hz, 1H), 7.17 (d, J=7.6 Hz, 1H), 5.71 (s, 2H), 4.62 (s, 2H), 3.60 (m, 2H), 3.32 (m, 2H), 1.75-1.71 (m, 4H); $^{13}$C NMR (75 MHz, CDCl$_3$): δ/ppm 159.5, 153.4, 147.5, 146.1, 138.2, 137.0, 126.3, 124.4, 121.8, 121.4, 121.3, 73.7, 70.7, 56.0, 51.4, 27.1, 26.0; m.p.: 49-50° C.; HRMS (ESI$^+$): calcd. (C$_{19}$H$_{20}$N$_8$O$_3$+H$^+$) 409.1736, found 409.1733.

Example 6

Preparation of Monotriazole T2

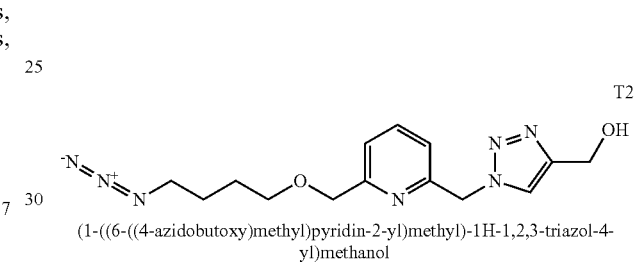

(1-((6-((4-azidobutoxy)methyl)pyridin-2-yl)methyl)-1H-1,2,3-triazol-4-yl)methanol $^1$H NMR (300 MHz, CDCl$_3$): δ/ppm 7.69 (t, J=7.8 Hz, 1H); 7.69 (s, 1H), 7.39 (d, J=7.7 Hz, 1H), 7.06 (d, J=7.7 Hz, 1H), 5.62 (s, 2H), 4.80 (d, J=5.8 Hz, 2H), 4.60 (s, 2H), 3.59 (m, 2H), 3.32 (m, 2H), 2.62 (t, J=5.9 Hz, 1H), 1.76-1.71 (m, 4H); $^{13}$C NMR (75 MHz, CDCl$_3$): δ/ppm 159.3, 153.9, 148.2, 138.1, 122.4, 121.2, 121.1, 73.7, 70.7, 56.8, 55.8, 51.5, 27.1, 26.0; HRMS (ESI$^+$): calcd. (C$_{14}$H$_{19}$N$_7$O$_2$+Na$^+$) 340.1498 found 340.1496.

Example 7

Preparation of Monotriazole T3

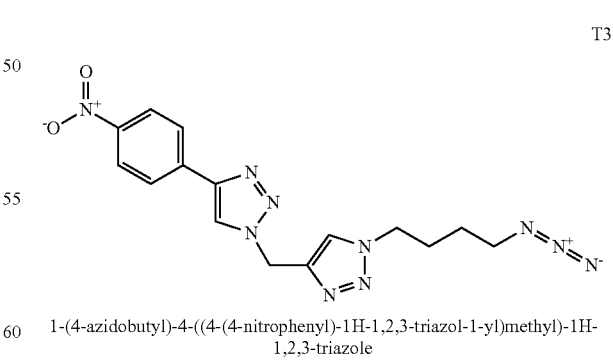

1-(4-azidobutyl)-4-((4-(4-nitrophenyl)-1H-1,2,3-triazol-1-yl)methyl)-1H-1,2,3-triazole $^1$H NMR (300 MHz, CDCl$_3$): δ/ppm 8.26 (d, J=8.6 Hz, 2H), 8.13 (s, 1H), 7.97 (d, J=8.8 Hz, 2H), 7.69 (s, 1H), 5.74 (s, 2H), 4.41 (t, J=7.1 Hz, 2H), 3.33 (t, J=6.5 Hz, 2H), 2.06-1.96 (m, 2H), 1.65-1.55 (m, 2H); $^{13}$C NMR (75 MHz, CDCl$_3$): δ/ppm 147.4, 146.1, 141.4, 136.8, 126.2, 124.4, 123.2, 121.6, 50.7, 50.1, 45.6, 27.5, 25.9; m.p.: 102-103° C.; HRMS (ESI+): calcd. (C$_{15}$H$_{16}$N$_{10}$O$_2$+Na+) 391.1355 found 391.1352.

Example 8

Preparation of Monotriazole T4

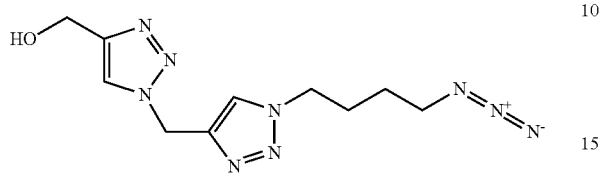

(1-((1-(4-azidobutyl)-1H-1,2,3-triazol-4-yl)methyl)-1H-1,2,3-triazol-4-yl)methanol $^1$H NMR (500 MHz, CDCl$_3$): δ/ppm 7.71 (s, 1H), 7.63 (s, 1H), 5.64 (s, 2H), 4.75 (d, J=5.1 Hz, 2H), 4.38 (t, J=7.1 Hz, 2H), 3.33 (t, J=6.6 Hz, 2H), 3.19 (t, J=5.5 Hz, 1H), 2.03-1.97 (m, 2H), 1.62-1.57 (m, 2H); $^{13}$C NMR (125 MHz, CDCl$_3$): δ/ppm 148.3, 141.9, 123.2, 122.3, 56.3, 50.7, 50.1, 45.4, 27.5, 25.9; m.p.: 70-71° C.; HRMS (ESI+): calcd. (C$_{10}$H$_{15}$N$_9$O+Na+) 300.1297 found 300.1291.

Example 9

Preparation of Monotriazole T5

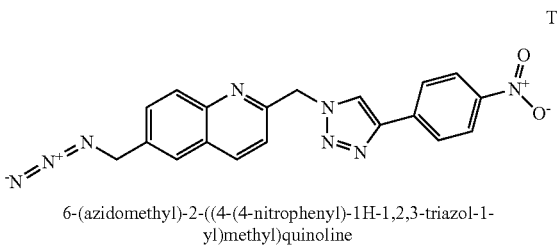

6-(azidomethyl)-2-((4-(4-nitrophenyl)-1H-1,2,3-triazol-1-yl)methyl)quinoline $^1$H NMR (300 MHz, CDCl$_3$): δ/ppm 8.27 (d, J=8.9 Hz, 2H), 8.20 (d, J=8.4 Hz, 1H), 8.12-8.10 (m, 2H), 8.00 (d, J=8.8 Hz, 2H), 7.79 (s, 1H), 7.72 (dd, J=1.8, 8.7 Hz, 1H), 7.43 (d, J=8.5 Hz, 1H), 5.92 (s, 2H), 4.56 (s, 2H); $^{13}$C NMR (75 MHz, CDCl$_3$): δ/ppm 154.6, 147.7, 147.6, 146.4, 138.0, 136.9, 134.9, 130.4, 130.3, 127.6, 126.8, 126.4, 124.5, 121.9, 120.5, 56.7, 54.6; m.p.: 140-142° C.; HRMS (ESI+): calcd. (C$_{19}$H$_{14}$N$_8$O$_2$+H+) 387.1318 found 387.1314.

Example 10

Preparation of Monotriazole T6

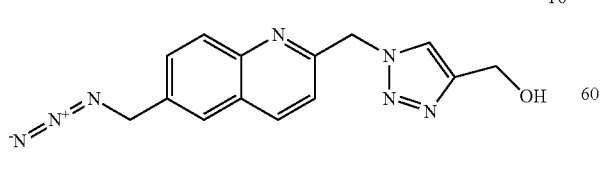

(1-((6-(azidomethyl)quinolin-2-yl)methyl)-1H-1,2,3-triazol-4-yl)methanol $^1$H NMR (500 MHz, CDCl$_3$): δ/ppm 8.16 (d, J=8.5 Hz, 1H), 8.09 (d, J=8.7 Hz, 1H), 7.77 (s, 1H), 7.72 (s, 1H), 7.70 (d, J=8.7 Hz, 1H), 7.32 (d, J=8.5 Hz, 1H), 5.84 (s, 2H), 4.81 (d, J=5.2 Hz, 2H), 4.56 (s, 2H); $^{13}$C NMR (125 MHz, CDCl$_3$): δ/ppm 154.9, 148.2, 147.4, 137.8, 134.6, 130.2, 130.1, 127.4, 126.7, 122.4, 120.3, 56.7, 56.3, 54.5; m.p.: 123-125° C.; HRMS (ESI+): calcd. (C$_{14}$H$_{13}$N$_7$O+H+) 296.1260 found 296.1255.

Example 11

Preparation of Monotriazole T7

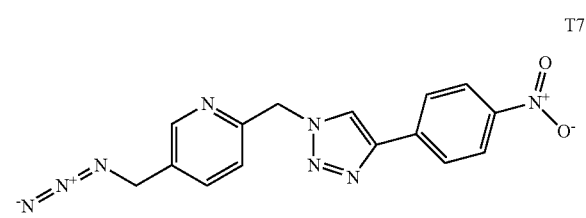

5-(azidomethyl)-2-((4-(4-nitrophenyl)-1H-1,2,3-triazol-1-yl)methyl)pyridine $^1$H NMR (500 MHz, CDCl$_3$): δ/ppm 8.57 (s, 1H), 8.28 (d, J=9.0 Hz, 2H), 8.13 (s, 1H), 8.00 (d, J=9.0 Hz, 2H), 7.71 (d, J=8.0 Hz, 1H), 7.36 (d, J=8.0 Hz, 1H), 5.74 (s, 2H), 4.42 (s, 2H); $^{13}$C NMR (125 MHz, CDCl$_3$): δ/ppm 154.1, 149.6, 147.5, 146.3, 137.4, 137.0, 131.7, 126.4, 124.5, 122.9, 122.0, 55.6, 51.9; m.p.: 128-129° C.; HRMS (ESI+): calcd. (C$_{15}$H$_{12}$N$_8$O$_2$+H+) 337.1161 found 337.1157.

Example 11

Preparation of Monotriazole T8

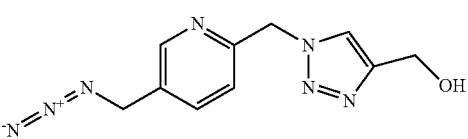

(1-((5-(azidomethyl)pyridin-2-yl)methyl)-1H-1,2,3-triazol-4-yl)methanol $^1$H NMR (500 MHz, CDCl$_3$): δ/ppm 8.53 (s, 1H), 7.72 (s, 1H), 7.67 (d, J=8.0 Hz, 1H), 7.24 (d, J=8.0 Hz, 1H), 5.65 (s, 2H), 4.78 (d, J=1.9 Hz, 2H), 4.40 (s, 2H); $^{13}$C NMR (125 MHz, CDCl$_3$): δ/ppm 154.5, 149.3, 137.6, 137.4, 131.5, 122.8, 56.7, 55.4, 51.9; HRMS (ESI+): calcd. (C$_{10}$H$_{11}$N$_7$O+Na+) 268.0923 found 268.0923.

Example 12

Second Click Reaction to Prepare Bistriazole TT1

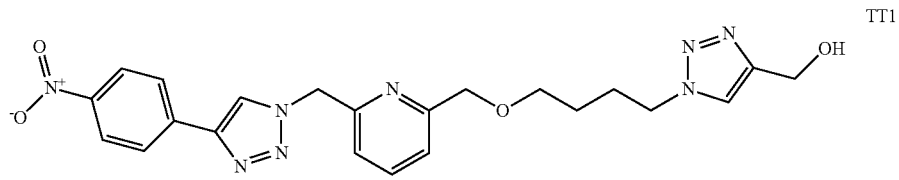

(1-(4-((6-((4-(4-nitrophenyl)-1H-1,2,3-triazol-1-yl)-methyl)pyridin-2-yl)methoxy)butyl)-1H-1,2,3-triazol-4-yl)methanol The general procedure described in this Example 12 was used to prepare bistriazoles TT2 through TT8 in the following examples 13-19. Compound T1 (40.8 mg, 0.10 mmol) and propargyl alcohol (5.6 mg, 0.10 mmol) were added into a mixed solvent of $CH_3OH$ (0.25 mL) and $CH_2Cl_2$ (0.25 mL), or a HEPES buffer solution (0.5 mL, pH=7.0), followed by the addition of NaAsc (4.0 mg, 20 mmol) and $Cu(OAc)_2$ (25 µL, 0.4 M in $H_2O$, 10 mmol). The reaction mixture was stirred at rt for 12 h before being diluted with $CH_2Cl_2$ and purified by silica column chromatography, to afford compound TT1 (40.4 mg, 87%). $^1$H NMR (500 MHz, DMSO-$d_6$): δ/ppm 8.90 (s, 1H), 8.30 (d, J=8.8 Hz, 2H), 8.14 (d, J=8.8 Hz, 2H), 7.93 (s, 1H), 7.85 (t, J=7.8 Hz, 1H), 7.39 (d, J=7.7 Hz, 1H), 7.24 (d, J=7.7 Hz, 1H), 5.78 (s, 2H), 5.11 (t, J=5.5 Hz, 1H), 4.51-4.50 (m, 4H), 4.33 (t, J=7.1 Hz, 2H), 3.49 (t, J=6.3 Hz, 2H), 1.89-1.84 (m, 2H), 1.54-1.48 (m, 2H); $^{13}$C NMR (125 MHz, DMSO-$d_6$): δ/ppm 158.5, 153.9, 147.8, 146.6, 144.5, 138.0, 137.0, 125.9, 124.3, 124.2, 122.5, 120.9, 120.5, 72.7, 69.4, 55.0, 54.6, 48.9, 26.7, 26.0; m.p.: 125-127° C.; HRMS (ESL): calcd. ($C_{22}H_{24}N_8O_4$+$Na^+$) 487.1818 found 487.1827.

Example 13

Second Click Reaction to Prepare Bistriazole TT2

TT2

(1-((6-((4-(4-(4-nitrophenyl)-1H-1,2,3-triazol-1-yl)butoxy)methyl)pyridin-2-yl)-methyl)-1H-1,2,3-triazol-4-yl)methanol $^1$H NMR (500 MHz, DSMO-$d_6$): δ/ppm 8.84 (d, J=1.8 Hz, 1H), 8.30 (dd, J=1.8, 6.9 Hz, 2H), 8.10 (dd, J=1.8, 6.9 Hz, 2H), 8.01 (s, 1H), 7.80 (t, J=7.7 Hz, 1H), 7.37 (d, J=7.8 Hz, 1H), 7.09 (d, J=7.7 Hz, 1H), 5.65 (s, 2H), 5.17-5.14 (m, 1H), 4.53-4.52 (m, 4H), 4.47 (t, J=7.1 Hz, 2H), 3.54 (t, J=6.3 Hz, 2H), 2.01-1.95 (m, 2H), 1.62-1.59 (m, 2H); $^{13}$C NMR (125 MHz, DMSO-$d_6$): δ/ppm 158.4, 154.6, 148.2, 146.5, 144.3, 137.9, 137.2, 125.8, 124.3, 123.4, 123.3, 120.6, 120.4, 72.7, 69.5, 55.0, 54.3, 49.5, 26.5, 26.1; m.p.: 132-133° C.; HRMS (ESI): calcd. ($C_{22}H_{24}N_8O_4$+$Na^+$) 487.1818 found 487.1824.

Example 14

Second Click Reaction to Prepare Bistriazole TT3

TT3

(1-(4-(4-((4-(4-nitrophenyl)-1H-1,2,3-triazol-1-yl)-methyl)-1H-1,2,3-triazol-1-yl)butyl)-1H-1,2,3-triazol-4-yl)methanol $^1$H NMR (300 MHz, DMSO-$d_6$): δ/ppm 8.87 (s, 1H), 8.31 (d, J=8.9 Hz, 2H), 8.23 (s, 1H), 8.13 (d, J=9.0 Hz, 2H), 7.95 (s, 1H), 5.77 (s, 2H), 5.14 (t, J=5.7 Hz, 1H), 4.49 (d, J=5.5 Hz, 2H), 4.40-4.36 (m, 4H), 1.77 (s, 4H); $^{13}$C NMR (75 MHz, DMSO-$d_6$): δ/ppm 147.9, 146.6, 144.6, 141.1, 136.9, 125.9, 124.2, 124.1, 123.5, 122.5, 55.0, 48.7, 48.4, 44.9, 26.8, 26.7; m.p.: 171-173° C.; HRMS (ESI$^+$): calcd. ($C_{18}H_{20}N_{10}O_3$+$Na^+$) 447.1618, found 447.1613.

Example 15

Second Click Reaction to Prepare Bistriazole TT4

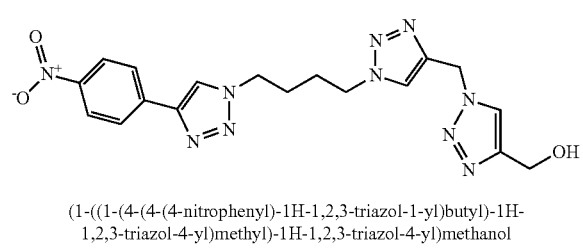

(1-((1-((4-(4-nitrophenyl)-1H-1,2,3-triazol-1-yl)butyl)-1H-1,2,3-triazol-4-yl)methyl)-1H-1,2,3-triazol-4-yl)methanol $^1$H NMR (500 MHz, DMSO-$d_6$): δ/ppm 8.84 (s, 1H), 8.32 (d, J=7.0 Hz, 2H), 8.19 (s, 1H), 8.11 (d, J=7.0 Hz, 2H), 7.96 (s, 1H), 5.65 (s, 2H), 5.18 (s, 1H), 4.49-4.46 (m, 4H), 4.41 (t, J=6.5 Hz, 2H), 1.84 (m, 4H); $^{13}$C NMR (125 MHz, DMSO-$d_6$): δ/ppm 148.3, 146.6, 144.4, 141.7, 137.2, 125.9, 124.4, 124.1, 123.6, 122.7, 55.0, 49.1, 48.8, 44.4, 26.8, 26.7; m.p.: 170-172° C.; HRMS (ESI$^+$): calcd. ($C_{18}H_{20}N_{10}O_3$+Na$^+$) 447.1618, found 447.1610.

Example 16

Second Click Reaction to Prepare Bistriazole TT5

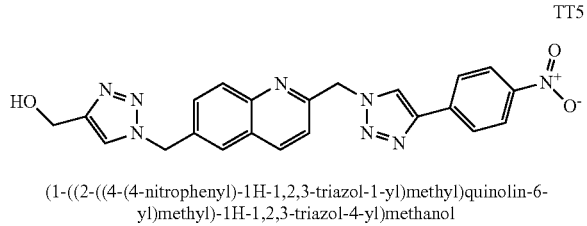 [SMILES: O=[N+]([O-])c1ccc(-c2cn(Cc3ccc4cc(Cn5cc(CO)nn5)ccc4n3)nn2)cc1]

(1-((2-((4-(4-nitrophenyl)-1H-1,2,3-triazol-1-yl)methyl)quinolin-6-yl)methyl)-1H-1,2,3-triazol-4-yl)methanol $^1$H NMR (500 MHz, DMSO-$d_6$): δ/ppm 8.97 (s, 1H), 8.42 (d, J=8.5 Hz, 1H), 8.31 (d, J=8.7 Hz, 2H), 8.15 (d, J=8.6 Hz, 2H), 8.06 (s, 1H), 7.97 (d, J=8.6 Hz, 1H), 7.90 (s, 1H), 7.69 (d, J=8.6 Hz, 1H), 7.50 (d, J=8.5 Hz, 1H), 6.01 (s, 2H), 5.78 (s, 2H), 5.13 (s, 1H), 4.51 (s, 2H); $^{13}$C NMR (125 MHz, DMSO-$d_6$): δ/ppm 155.6, 148.3, 146.6, 146.5, 144.6, 137.6, 137.0, 134.8, 129.8, 129.2, 127.0, 126.9, 126.0, 124.5, 124.3, 123.0, 120.5, 55.2, 55.0, 52.4; HRMS (ESI$^+$): calcd. ($C_{22}H_{18}N_8O_3$+Na$^+$) 465.1400, found 465.1386.

Example 17

Second Click Reaction to Prepare Bistriazole TT6

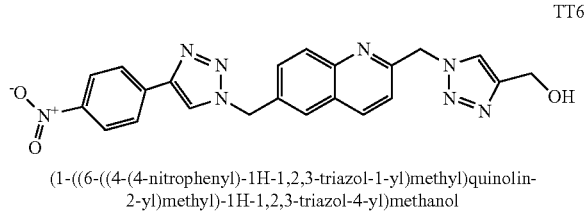

(1-((6-((4-(4-nitrophenyl)-1H-1,2,3-triazol-1-yl)methyl)quinolin-2-yl)methyl)-1H-1,2,3-triazol-4-yl)methanol $^1$H NMR (500 MHz, DMSO-$d_6$): δ/ppm 8.96 (s, 1H), 8.42 (d, J=8.6 Hz, 1H), 8.31 (d, J=8.9 Hz, 2H), 8.13 (d, J=8.9 Hz, 2H), 8.12 (s, 1H), 8.00 (d, J=8.8 Hz, 1H), 7.95 (s, 1H), 7.76 (d, J=8.8 Hz, 1H), 7.36 (d, J=8.6 Hz, 1H), 5.91 (s, 2H), 5.89 (s, 2H), 5.21 (t, J=5.6 Hz, 1H), 4.53 (d, J=5.5 Hz, 2H); $^{13}$C NMR (125 MHz, DMSO-$d_6$): δ/ppm 157.5, 149.4, 147.8, 145.9, 138.8, 138.2, 135.3, 131.0, 130.5, 128.3, 128.0, 127.1, 125.5, 125.0, 124.9, 121.5, 56.2, 56.0, 54.1; HRMS (ESI$^+$): calcd. ($C_{22}H_{18}N_8O_3$+H$^+$) 443.1580, found 443.1578.

Example 18

Second Click Reaction to Prepare Bistriazole TT7

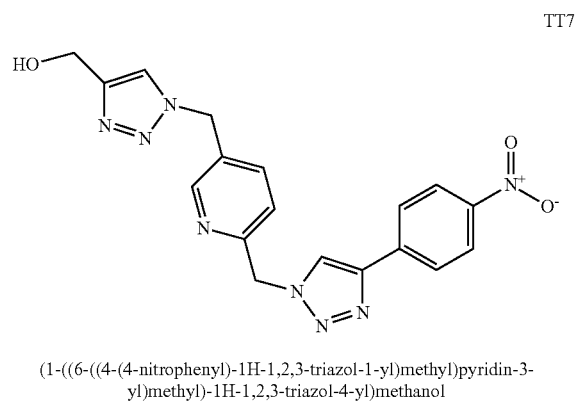 [SMILES: O=[N+]([O-])c1ccc(-c2cn(Cc3ccc(Cn4cc(CO)nn4)cn3)nn2)cc1]

(1-((6-((4-(4-nitrophenyl)-1H-1,2,3-triazol-1-yl)methyl)pyridin-3-yl)methyl)-1H-1,2,3-triazol-4-yl)methanol $^1$H NMR (500 MHz, DMSO-$d_6$): δ/ppm 8.93 (s, 1H), 8.57 (s, 1H), 8.31 (d, J=9.0 Hz, 2H), 8.14 (d, J=9.0 Hz, 2H), 8.07 (s, 1H), 7.79 (d, J=8.1 Hz, 1H), 7.41 (d, J=8.1 Hz, 1H), 5.81 (s, 2H), 5.63 (s, 2H), 5.17 (t, J=5.6 Hz, 1H), 4.48 (d, J=5.6 Hz, 2H); $^{13}$C NMR (125 MHz, DMSO-$d_6$): δ/ppm 154.6, 149.2, 148.5, 146.6, 144.6, 137.2, 137.1, 131.6, 126.0, 124.5, 124.4, 123.0, 122.4, 55.0, 54.4, 49.9; m.p.: 220-221° C.; HRMS (ESI): calcd. ($C_{18}H_{16}N_8O_3$+Na$^+$) 415.1243, found 415.1252.

Example 19

Second Click Reaction to Prepare Bistriazole TT8

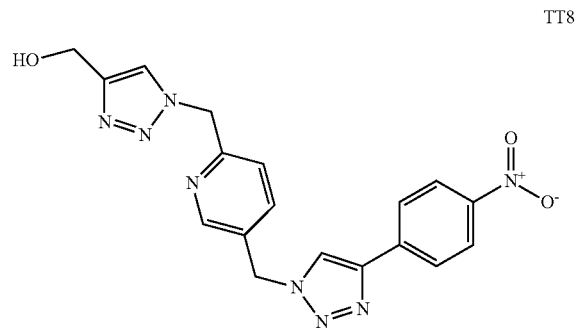

(1-((5-((4-(4-nitrophenyl)-1H-1,2,3-triazol-1-yl)methyl)pyridin-2-yl)methyl)-1H-1,2,3-triazol-4-yl)methanol $^1$H NMR (500 MHz, DMSO-$d_6$): δ/ppm 8.93 (s, 1H), 8.64 (s, 1H), 8.31 (d, J=9.0 Hz, 2H), 8.11 (d, J=9.0 Hz, 2H), 8.03 (s, 1H), 7.82 (d, J=8.1 Hz, 1H), 7.31 (d, J=8.1 Hz, 1H), 5.75 (s, 2H), 5.70 (s, 2H), 5.19 (t, J=5.6 Hz, 1H), 4.50 (d, J=5.6 Hz, 2H); $^{13}$C NMR (125 MHz, DMSO-$d_6$): δ/ppm 155.4, 149.2, 148.2, 146.7, 144.9, 137.3, 137.0, 130.8, 126.0, 124.4, 123.8, 123.6, 122.3, 55.0, 54.0, 50.4; m.p.: 249-250° C.; HRMS (ESI$^+$): calcd. ($C_{18}H_{16}N_8O_3$+Na$^+$) 415.1243, found 415.1245.

Example 20

General Procedure for the Preparation of Bistriazoles (TT1-TT8) Using the One-Pot, Successive Double-Click Reaction Bisazides 4 (26.4 mg, 0.10 mmol) and 1-ethynyl-4-nitrobenzene (15.1 mg, 0.10 mmol) were added to a 2-dram sample vial, along with a mixed solvent of $CH_3OH$ (0.25 mL) and $CH_2Cl_2$ (0.25 mL), or a HEPES buffer solution (0.5 mL, pH=7.0). A solution of $Cu(OAc)_2$ (25 µL, 0.4 M in $H_2O$, 10 µmol) was added subsequently. The reaction mixture was capped and stirred at rt. The reaction progress was monitored by TLC (50/50 $CH_2Cl_2$/EtOAc). After the disappearance of the starting material spot (5 h), propargyl alcohol (5.6 mg, 0.10 mmol) and NaAsc (4.0 mg, 20 µmol) were added. The reaction mixture was stirred for another 12 h, before being diluted with $CH_2Cl_2$. The product was chromatographed on silica gel using $CH_3OH$ in $CH_2Cl_2$ (up to 5%) to afford TT1 (45.1 mg, 97%).

Example 21

General Procedure for the Preparation of Bistriazoles (TT7, TT9 and TT10) Using the One-Pot, Three-Component Double-Click Reactions 1-Ethynyl-4-nitrobenzene (15.1 mg, 0.10 mmol), propargyl alcohol (5.6 mg, 0.10 mmol), bisazides 7 (18.9 mg, 0.10 mmol), and $CH_3CN$ (0.5 mL) were added to a 2-dram sample vial. A solution of $Cu(OAc)_2$ (25 µL, 0.4 M in $H_2O$, 10 µmol) was subsequently added. The reaction mixture was capped and stirred at rt, the progress of which was monitored by TLC (50/50 $CH_2Cl_2$/EtOAc). After the disappearance of the starting material spot (5 h), NaAsc (4.0 mg, 20 µmol) was added. The solution was stirred for another 12 h. The solution was diluted with $CH_2Cl_2$ and the crude product was chromatographed on silica gel using $CH_3OH$ in $CH_2Cl_2$ (up to 5%) to afford TT7 (27.4 mg, 70%).

Example 22

Preparation of Bistriazole TT9

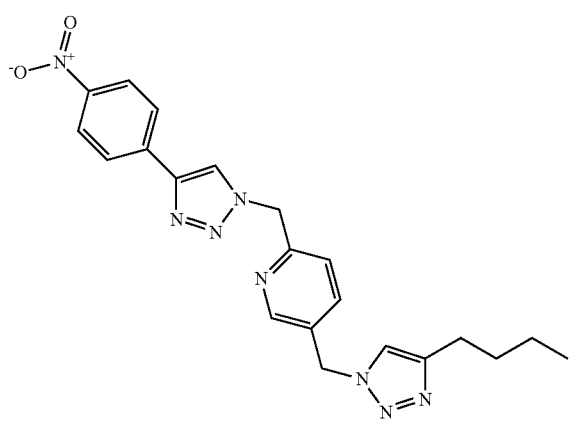

5-((4-butyl-1H-1,2,3-triazol-1-yl)methyl)-2-((4-(4-nitrophenyl)-1H-1,2,3-triazol-1-yl)methyl)pyridine $^1$H NMR (500 MHz, DMSO-$d_6$): δ/ppm 8.56 (s, 1H), 8.28 (d, J=8.8 Hz, 2H), 8.11 (s, 1H), 8.00 (d, J=8.8 Hz, 2H), 7.61 (d, J=8.1 Hz, 1H), 7.33 (d, J=8.1 Hz, 1H), 7.24 (s, 1H), 5.72 (s, 2H), 5.53 (s, 2H), 2.69 (t, J=7.7 Hz, 2H), 1.62 (m, 2H), 1.35 (m, 2H), 0.91 (t, J=7.3 Hz, 3H); $^{13}$C NMR (125 MHz, DMSO-$d_6$): δ/ppm 154.5, 149.6, 149.3, 147.5, 146.2, 137.2, 136.9, 131.2, 126.3, 124.5, 123.0, 122.1, 120.8, 55.5, 51.0, 31.6, 25.5, 22.5, 14.0; m.p.: 150-151° C.; HRMS (ESI$^+$): calcd. ($C_{21}H_{22}N_8O_2$+Na$^+$) 441.1763, found 441.1757.

Example 23

Preparation of Bistriazole TT10

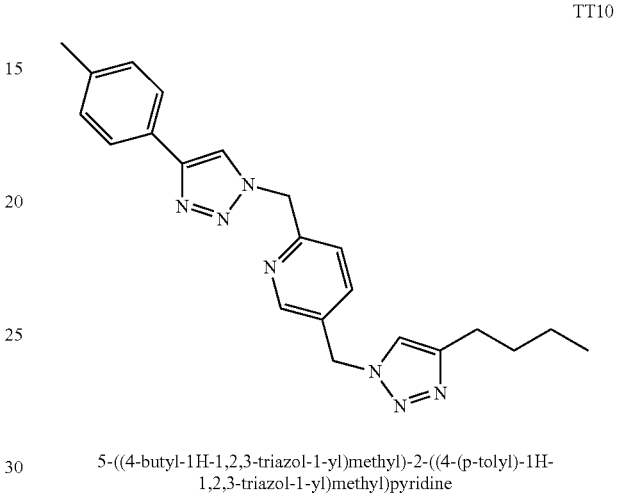

5-((4-butyl-1H-1,2,3-triazol-1-yl)methyl)-2-((4-(p-tolyl)-1H-1,2,3-triazol-1-yl)methyl)pyridine $^1$H NMR (500 MHz, DMSO-$d_6$): δ/ppm 8.55 (s, 1H), 7.89 (s, 1H), 7.72 (d, J=8.1 Hz, 2H), 7.58 (d, J=8.0 Hz, 1H), 7.25 (d, J=8.0 Hz, 1H), 7.24 (s, 1H), 7.23 (d, J=7.9 Hz, 2H), 5.70 (s, 2H), 5.53 (s, 2H), 2.69 (t, J=7.7 Hz, 2H), 2.38 (s, 3H), 1.62 (m, 2H), 1.36 (m, 2H), 0.91 (t, J=7.4 Hz, 3H); $^{13}$C NMR (125 MHz, DMSO-$d_6$): δ/ppm 155.3, 149.1, 148.6, 138.4, 137.2, 131.0, 129.7, 127.7, 125.8, 122.9, 120.7, 120.1, 55.5, 51.1, 31.6, 25.5, 22.5, 21.5, 14.0; HRMS (ESI$^+$): calcd. ($C_{22}H_{25}N_7$+Na$^+$) 410.2069, found 410.2063.

Example 24

Procedure for Preparing the Single Crystals for X-Ray Diffraction

Synthesis of complex [$Cu_2(7)_2Cl_4$]. (Warning! Low molecular weight organic azides are potentially explosive. Appropriate protection measures should always be taken when handling these compounds.) Solutions of $CuCl_2$ (26.8 mg, 0.16 mmol) and bisazide 7 (59.5 mg, 0.32 mmol) were mixed in $CH_3CN$ (5 mL). The solvent was removed under reduced pressure. The resulting deep green solid was washed with diethyl ether (3×10 mL). The solid was dissolved in $CH_3CN$ (3 mL), filtered through a piece of glass microfiber, and set up in vapor diffusion chambers with diethyl ether. After 3-4 days, green crystals suitable for X-ray diffraction formed.

Example 25

Representative Procedure of the $^1$H NMR Kinetic Assay

Stock solutions of bisazide 7 (100 mM) in $CD_3CN$, 1-ethynyl-4-nitrobenzene (100 mM) in $CD_3CN$, 1-hexyne (100 mM) in CD$_3$CN, Cu(OAc)$_2$.H$_2$O (100 mM) in D$_2$O, and sodium ascorbate (200 mM) in D$_2$O were prepared. The stock solutions of 7 (100 μL), 1-ethynyl-4-nitrobenzene (100 μL), 1-hexyne (100 μL), Cu(OAc)$_2$.H$_2$O (10 μL), and CD$_3$CN (690 μL) were added sequentially via syringes to a vial. The combined solution was mixed for ~10 sec before being transferred to an NMR tube (total volume ~0.6 mL). The reaction progress was monitored on a 500 MHz instrument. The data was collected every 5 min at 22° C. After the first CuAAC reaction was completed, NaAsc (10 mL) was added into the NMR tube. No further reaction was observed for the next 12 h.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of preparing a bis-triazole compound, the method comprising:
   contacting a bis-azide compound and a first alkyne to thereby prepare an intermediate mono-azide/mono-azole compound; and
   contacting the intermediate mono-azide/mono-azole compound with a second alkyne to thereby prepare the bis-triazole compound,
   wherein the bis-azide comprises a chelating azide and a non-chelating azide, and further wherein the first alkyne selectively reacts with the chelating azide.

2. The method of claim 1 wherein the bis-azide compound and the first alkyne compound are contacted in the presence of a catalyst.

3. The method of claim 2 wherein the catalyst comprises Cu(II) ions.

4. The method of claim 1 wherein the intermediate mono-azide/mono-azole compound and the second alkyne compound are contacted in the presence of a catalyst.

5. The method of claim 4 wherein the catalyst comprises Cu(I) ions.

6. The method of claim 1 wherein greater than 50% of the first alkyne reacts with the chelating azide of the bis-azide compound.

7. The method of claim 1 wherein greater than 80% of the first alkyne reacts with the chelating azide of the bis-azide compound.

8. The method of claim 1 wherein greater than 95% of the first alkyne reacts with the chelating azide of the bis-azide compound.

9. The method of claim 1 wherein the bis-azide has one of the following general structures:

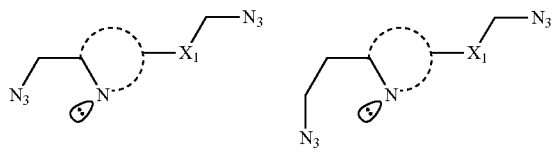

wherein:
   the dashed circle represents a structural entity that supports a Lewis basic nitrogen atom (shown with a pair of electrons) and links two azido groups; and
   $X_1$ represents an aliphatic linking moiety or a direct link to the structural support entity.

10. The method of claim 9 wherein the structural entity that supports the Lewis basic nitrogen atom is selected from the group consisting of pyridine, pyrimidine, pyrazine, pyridazine, triazines, pyrrole, pyrazole, imidazole, triazoles, quinoline, isoquinoline, cinnoline, quinazoline, quinoxaline, naphthyridines, indole, indazoles, benzoimidazole, benzotriazoles, pyrrolopyridines, pyrazolopyridines, imidazopyridines, triazolopyridines, pyrrolopyridazines, pyrazolopyridazines, imidazopyridazines, triazolopyridazines, pyrrolopyrimidines, pyrazolopyrimidines, purines, triazolopyrimidines, pyrrolopyrazines, pyrazolopyrazines, imidazopyrazines, triazolopyrazines, and combinations thereof.

11. The method of claim 9 wherein the $X_1$ aliphatic linking moiety comprises a direct bond between the methylene attached to the non-chelating azido group or from one to 12 carbon atoms.

12. The method of claim 1 wherein the first alkyne, the second alkyne, or both has the general structure:

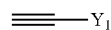

wherein $Y_1$ represents a functional group.

* * * * *